US006553317B1

(12) United States Patent
Lincoln et al.

(10) Patent No.: US 6,553,317 B1
(45) Date of Patent: Apr. 22, 2003

(54) RELATIONAL DATABASE AND SYSTEM FOR STORING INFORMATION RELATING TO BIOMOLECULAR SEQUENCES AND REAGENTS

(75) Inventors: Stephen E. Lincoln, Redwood City, CA (US); Tod M. Klingler, San Carlos, CA (US); Landes C. Wong, Milpitas, CA (US); Scott R. Panzer, Sunnyvale, CA (US); David M. Hodgson, Palo Alto, CA (US); Laura Y. Ito, Pleasanton, CA (US); Andrew D. Ament, Clayton, MO (US); Richard Cathcart, Redwood City, CA (US); Helen E. Jolley, San Leandro, CA (US); Ingrid E. Akerblom, Redwood City, CA (US); Brian M. McKelligon, Mountain View, CA (US); Mayank K. Thanawala, Mountain View, CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/034,807

(22) Filed: Mar. 4, 1998

Related U.S. Application Data

(63) Continuation-in-part of application No. 08/947,845, filed on Oct. 9, 1997.
(60) Provisional application No. 60/040,033, filed on Mar. 5, 1997, and provisional application No. 60/076,682, filed on Mar. 3, 1998.

(51) Int. Cl.[7] ............................................... G01N 33/48
(52) U.S. Cl. .............................. 702/20; 435/6; 702/19; 707/10; 707/104
(58) Field of Search .............................. 435/6; 707/104, 707/10; 702/19–20

(56) References Cited

U.S. PATENT DOCUMENTS

| 4,487,835 A | * | 12/1984 | Uhlin et al. ................. 435/317 |
| 5,523,208 A | | 6/1996 | Kohler et al. .................. 435/6 |
| 5,706,498 A | | 1/1998 | Fujimiya et al. ................ 435/6 |
| 5,840,484 A | | 11/1998 | Seilhamer et al. .............. 435/6 |
| 5,953,727 A | * | 9/1999 | Maslyn et al. ............... 707/104 |
| 5,970,500 A | * | 10/1999 | Sabatini et al. .............. 707/104 |
| 6,110,426 A | * | 8/2000 | Shalon et al. ............... 422/68.1 |
| 6,363,399 B1 | * | 3/2002 | Maslyn et al. ............... 707/104 |

FOREIGN PATENT DOCUMENTS

WO    WO 96/23078    8/1996

OTHER PUBLICATIONS

Schena et al., Parallel human genome analysis: Microarray–based expression monitoring of 1000 genes; Proc. Natl. Acad. Sci. USA, vol. 93 pp 10614–10619, Oct. 1996 Biochemistry.*

D. W. Smith "Bio Computing: Informatics & Genome Projects." Academic Press pp. 51–117 & 233–267, 1993.*
Parsons et al. "Clustering cDNA Sequences". CABIOS, 8(5) 461–466, 1992.*
Cuticchia et al. "CMAP: Contig Mapping and Analysis Package, a Relational Database—"CABIOS 8(15) 467–474, 1992.*
The Institute for Genomic Research, TIGR Database. Internet—http://www.tigr.org (Downloaded Dec. 23, 1997).
National Center for Biotechnology Information (Index). Internet—http://www3.ncbi.nlm.nih.gov/ (Downloaded Dec. 23, 1997).
National Center for Biotechnology Information; ENTREZ. Internet—http://www3.ncbi.nlm.nih.gov/entrez (Downloaded Dec. 23, 1997).
National Center for Biotechnology Information; UniGene. Internet—http://www3.ncbi.nlm.nih.gov/unigene (Downloaded Dec. 23, 1997).
National Center for Biotechnology Information; GenBank. Internet—http://www3.ncbi.nlm.gov/web/genbank (Downloaded Dec. 23, 1997.).
MAGPIE; Automated Genome Project Investigation Environment. Internet—http://www.mcs.anl.gov/home/gaasterl/magpie.html (Downloaded Dec. 23, 1997).
Stanford University, Stanford Genomic Resources. Internet http://genome—www.stanford.edu.
Incyte Pharmaceuticals, LIFESEQ Version 4.2 Release Notes and Physical Data Model, Oct. 1996.
Incyte Pharmaceuticals, LIFESEQ Version 4.1 Release Notes and Physical Data Model, Jul. 1996.
Incyte Pharmaceuticals, LIFESEQ Version 3.4 Release Notes, Jan. 1996.
Incyte Pharmaceuticals, LIFESEQ Version 2.5 Release Notes, Jun. 1995.
Incyte Pharmaceuticals, LIFESEQ Version 3.0 Release Notes, Sep. 1995.
Incyte Pharmaceuticals, LIFESEQ Version 4.0 Release Notes, Apr. 1996.
Incyte Pharmaceuticals, *Introduction to the LIFESEQ Database*, Version 3.4, Jan. 1996.

(List continued on next page.)

Primary Examiner—Kenneth R. Horlick
Assistant Examiner—Young Kim
(74) *Attorney, Agent, or Firm*—Beyer Weaver & Thomas, LLP

(57) ABSTRACT

The present invention provides relational database systems for storing biomolecular sequence information together with biological annotations detailing the source of the sequence information, and associated reagent information. The acquisition, storage and access of reagent information associated with databased biomolecular sequence information is a particular advantage of the present invention. Such reagent information identifies genetic information and materials which may be made available to a user of the relational database system of the present invention for further application in research, therapeutic pharmaceutical development or other fields. The reagent information aspect of the present invention is preferably used in conjunction with a biomolecular sequence relational database system.

36 Claims, 20 Drawing Sheets

OTHER PUBLICATIONS

Incyte Pharmaceuticals, *LIFESEQ Training Manual*, Version 4.1, Jul. 1996.

Green, et al., "Ancient Conserved Regions in New Gene Sequences and the Protein Databases", *Science*, v. 259, n. 5102, p. 1711–1716.

http://wehih.wehi.edu.au/.

No Author, "Incyte Serves Up Information, part I", *In Vivo the Business & Medicine Report*, p. 32, ISSN: 0258–851X.

Martin, et al., "Accessing Genetics Databases", *Database*, v. 17, n. 1, p. 51(8), (1994).

* cited by examiner

Clone matching a public-domain gene

*Singleton-* single new sequence with match

*Cluster-* related (overlapping) clones sharing a match

*Master cluster-* related (non-overlapping) clones

Clone unique to Internal database

*Unique singleton-* no match in public domain or Internal database

*Unique-* cluster member with no match in public domain

300

L.S._Version

| | | | |
|---|---|---|---|
| Software Product | <pk> | CHAR(20) | not null |
| Software Version | <pk> | CHAR(15) | not null |
| DataRelMonthYear | | CHAR(10) | null |

304

Clone

| | | | |
|---|---|---|---|
| CloneID | <pk> | CHAR(10) | not null |
| Library_ID | <fk> | CHAR(10) | not null |
| Annot_SequenceID | <fk> | CHAR(11) | null |
| NumSeq | | INTEGER | not null |
| ProductScore | | INTEGER | not null |
| Hit_ID | | CHAR(8) | null |
| Hit_Type | | CHAR(1) | null |
| LogLikelihood | | INTEGER | null |
| Hit_DataSource | | CHAR(10) | null |
| Hit_Description_Short | | CHAR(10) | null |
| ExternalValue | | INTEGER | null |
| GA_Status | | CHAR(8) | null |

302

Library

| | | | |
|---|---|---|---|
| Library_ID | <pk> | CHAR(10) | not null |
| Usable | | INTEGER | not null |
| Tissue_Category | | INTEGER | not null |
| Lib_Description | | VARCHAR2(40) | not null |
| Lib_Comment | | LONG | not null |
| TissueID | <fk> | INTEGER | not null |

375

GA_Well

| | | | |
|---|---|---|---|
| LotID | <pk,fk> | CHAR(10) | not null |
| WellID | <pk> | CHAR(10) | not null |
| CloneID | <fk> | CHAR(10) | not null |
| Vector | | CHAR(10) | null |
| InsertionSite | | CHAR(20) | null |
| SequenceSizeCut | | CHAR(40) | null |

380

GA_LotInformation

| | | | |
|---|---|---|---|
| LotID | <pk> | CHAR(10) | not null |
| BarCode | | CHAR(16) | null |
| CustomerID | | CHAR(10) | not null |
| DataShipped | | DATE | not null |
| Comments | | TEXT | null |

*Fig. 3C*

LifeSeq GeneAlbum™
biology in silico

*Reagent Information Results*

Confidential -- Property of Incyte Pharmaceuticals, Inc.
LifeSeq GeneAlbum Version 1.1 Dec97

Reagent Information Results based on Lot ID(s): aaa

| Lot | Well | CloneID | Library | Mit ID | Mit Description | Data Source | BScore | pValue |
|---|---|---|---|---|---|---|---|---|
| AAA | a01 | 002623 | HMC1NOT01 | g180574 | Human o-kit gene. | gb102pri | 1843 | 3.8e-109 |
| AAA | a02 | 008806 | HMC1NOT01 | g2224564 | Human mRNA for KIAA0812 gene, parital ol | gb102pri | 501 | 1.1e-30 |
| AAA | a03 | 058323 | MUSCNOT01 | g34837 | Human MYF6 gene encoding a muscle determ | gb102pri | 1420 | 7.1e-170 |
| AAA | a04 | 268900 | HNT2NOT01 | g1088280 | Human pyruvate dehydrogenase kinase isoe | gb102pri | 1793 | 5.9e-141 |
| AAA | a05 | 336138 | EOSIMET02 | g1183913 | Human hemopoietic cell protein-tyrosine | gb102pri | 602 | 5.9e-81 |
| AAA | a06 | 475972 | MMLR2DI01 | g34444 | Human mRNA for lymphotoxin | gb102pri | 2461 | 1.1e-198 |
| AAA | a07 | 530608 | BRAINOT03 | g1809219 | Human K+ channel beta 2 subunit mRNA, co | gb102pri | 1790 | 7.6e-158 |
| AAA | a08 | 644667 | BRSTTUT02 | g36628 | Human mRNA for metalloprotease stromely | gb102pri | 1998 | 5.6e-209 |
| AAA | a09 | 764505 | LUNGNOT04 | g439602 | Human Rad mRNS, complete cds. | gb102pri | 1226 | 2.6e-141 |
| AAA | a10 | 880448 | THYRNOT02 | g1663725 | Human serine/threonine kinase MNE (mnb) | gb102pri | 662 | 3.9e-46 |
| AAA | a11 | 973318 | MUSCNOT02 | g508854 | Human (clone PWNTnT16) skeletal muscle T | gb102pri | 1433 | 6.5e-203 |

*Fig. 4E*

RELATIONAL DATABASE AND SYSTEM FOR STORING INFORMATION RELATING TO BIOMOLECULAR SEQUENCES AND REAGENTS

CROSS-REFERENCE TO RELATED APPLICATIONS

The present application claims priority to U.S. Provisional Patent Application Ser. No. 60/040,033 entitled RELATIONAL DATABASE FOR STORING BIOMOLECULAR SEQUENCE AND REAGENT INFORMATION, filed Mar. 5, 1997, and to U.S. Provisional Patent Application Ser. No. 60/076,682 entitled BIOMOLECULAR SEQUENCE AND REAGENT INFORMATION RELATIONAL DATABASES AND SYSTEMS, filed Mar. 3, 1998, both of which are herein incorporated by reference for all purposes.

The present application is also a continuation-in-part of U.S. patent application Ser. No. 08/947,845 entitled RELATIONAL DATABASE FOR STORING BIOMOLECULE INFORMATION, filed Oct. 9, 1997, the disclosure of which is herein incorporated by reference for all purposes.

BACKGROUND OF THE INVENTION

The present invention relates generally to relational databases for storing and retrieving biological information. More particularly the invention relates to systems and methods for providing sequences of biological molecules and associated reagents in a relational format allowing retrieval in a client-server environment.

Informatics is the study and application of computer and statistical techniques to the management of information. In genome projects, bioinformatics includes the development of methods to search databases quickly, to analyze nucleic acid sequence information, and to predict protein sequence and structure from DNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers can not and will not be able to avoid using computer resources to explore gene expression, gene sequencing, and molecular structure.

One use of bioinformatics involves studying genes differentially or commonly expressed in different tissues or cell lines (e.g. normal and cancerous tissue). Such expression information is of significant interest in pharmaceutical research. The sequence tag method involves generation a large number (e.g., thousands) of Expressed Sequence Tags ("ESTs") from cDNA libraries (each produced from a different tissue or sample). ESTs are partial transcript sequences that may cover different parts of the mRNA(s) of a gene, depending on cloning and sequencing strategy. Each EST includes about 100 to 300 nucleotides. If it is assumed that the number of tags is proportional to the abundance of transcripts in the tissue or cell type used to make the cDNA library, then any variation in the relative frequency of those tags, stored in computer databases, can be used to detect the differential expression of the corresponding genes.

To make EST information manipulation easy to perform and understand, sophisticated computer database systems have been developed. In one database system, developed by Incyte Pharmaceuticals, Inc. of Palo Alto, Calif., abundance levels of MRNA species expressed in a given sample are electronically recorded and annotated with information available from public sequence databases such as GenBank. The resulting information is stored in a relational database that may be employed to evaluate changes in gene expression caused by disease progression, pharmacological treatment, aging, etc.

While relational database systems such as those developed by Incyte Pharmaceuticals, Inc. provide great power and flexibility in analyzing gene expression information, this area of technology is still in its infancy and further improvements in relational database systems will help accelerate biological research for numerous applications.

SUMMARY OF THE INVENTION

The present invention provides relational database systems for storing biomolecular sequence information together with biological annotations detailing the source of the sequence information, and associated reagent information. The acquisition, storage and access of reagent information associated with databased biomolecular sequence information is a particular advantage of the present invention. Such reagent information identifies genetic information and materials which may be made available to a user of the relational database system of the present invention for further application in research, therapeutic pharmaceutical development or other fields. The reagent information aspect of the present invention is preferably used in conjunction with a biomolecular sequence relational database system.

The present invention provides a computer system including a relational database having records containing information identifying initial sequences of polynucleotide inserts of a plurality of clones, optionally, additional sequences of the polynucleotide inserts of a subset of the plurality of clones, and reagent specifications of the subset of clones. The system also includes a user interface allowing a user to selectively view information regarding the sequences and reagent specifications.

The present invention also provides a method, implemented on a computer system, for accessing information relating to one or more reagent clones. The method involves providing a relational database having records containing information identifying initial sequences of polynucleotide inserts of a plurality of clones, optionally, additional sequences of the polynucleotide inserts of a subset of the plurality of clones, and reagent specifications of the subset of clones. The method also involves entering, in a graphical user interface, a query relating to one or more of the sequences or reagent specifications, determining matches between the query entry and the information, and displaying the results of the determination.

In addition, the present invention provides a computer program product, comprising a computer-usable medium having computer-readable program code embodied thereon relating to a relational database having records containing information identifying initial sequences of polynucleotide inserts of a plurality of clones, optionally, additional sequences of the polynucleotide inserts of a subset of the plurality of clones, and reagent specifications of the subset of clones. The computer program product may also include computer-readable program code for effecting the following steps within a computing system: providing an interface for receiving a query relating to one or more reagent specifications, determining matches between the query entry and the information, and displaying the results of the determination.

The present invention further provides a reagent clone identified by a process, at least partially implemented on a computer system, for establishing a set of reagent clones. The process involves grouping initial sequences of polynucleotide inserts in a plurality of clones into a master cluster, assembling the initial sequences of the master cluster into one or more contiguous sequences, such that relationships of sequences to each other in the master cluster are elucidated, and nominating at least one clone represented by a master cluster as a reagent clone, according to specified priority criteria. A set of reagent clones may also be nominated according to such a method. The set of reagent clones may have a variety of uses including as hybridizable elements on a biological microarray.

These and other features and advantages of the invention will be described in more detail below with reference to the drawings.

BRIEF DESCRIPTION OF THE DRAWINGS

FIGS. 3A–F are detailed views of various sections of FIG. 3.

FIGS. 4A–G are representations of various HTML screens used in a user interface in accordance with a preferred embodiment of the present invention.

DETAILED DESCRIPTION OF THE PREFERRED EMBODIMENTS

Figure 1A:
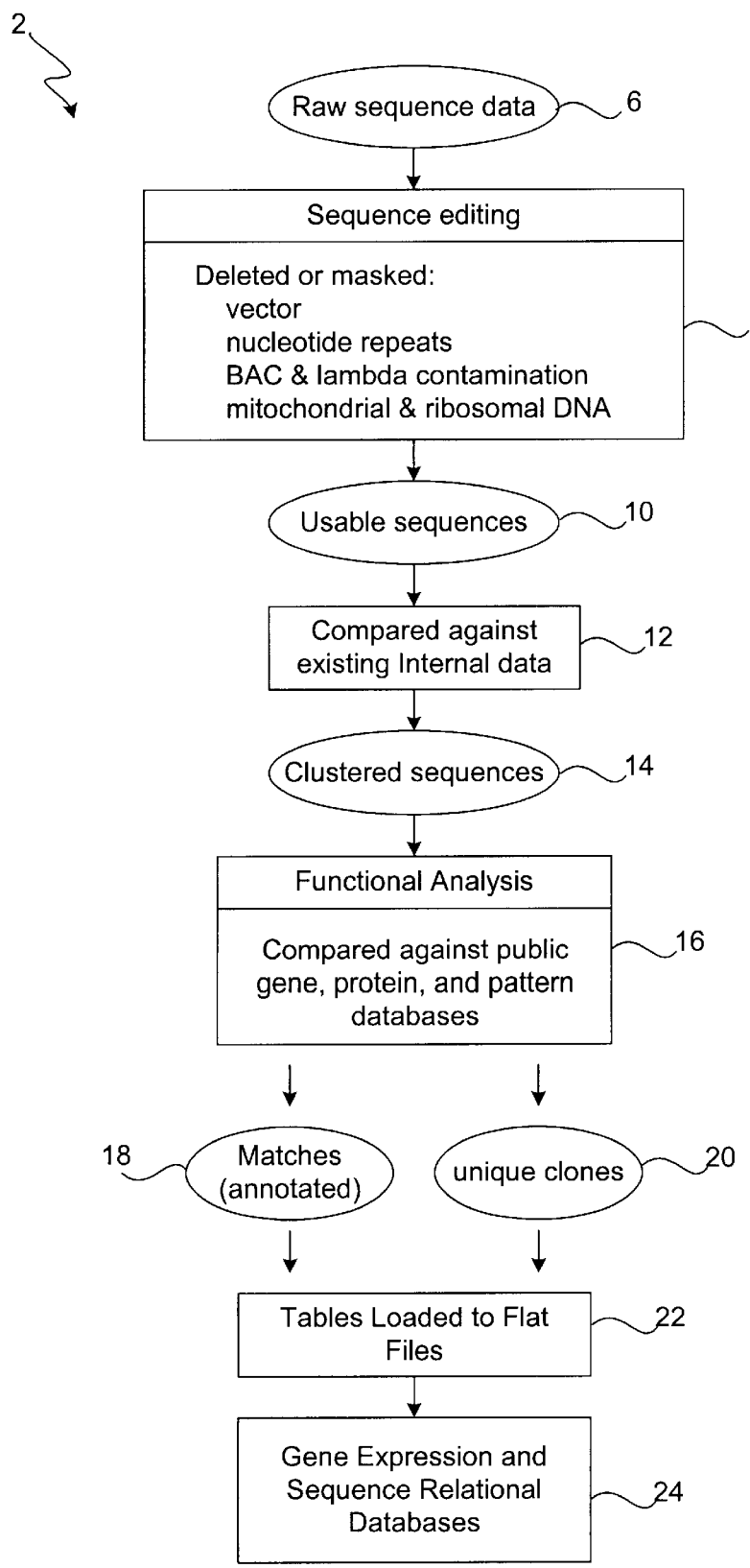
FIG. 1A is a flow diagram presenting key steps employed to generate a biomolecule database in accordance with one embodiment of the present invention.

Reference will now be made in detail to preferred embodiments of the invention. Examples of the preferred embodiments are illustrated in the accompanying drawings. While the invention will be described in conjunction with these preferred embodiments, it will be understood that it is not intended to limit the invention to such preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Generally, the present invention provides an improved relational database for storing biomolecular sequence information together with biological annotations detailing the source of the sequence information, and associated reagent information for select sequences. The invention may be employed to investigate biomolecular sequence data from various sources. For example, it may catalogue animal sequences (e.g., human, primate, rodent, amphibian, insect, etc.), plant sequences, and microbial sequences. The acquisition and storage of reagent information associated with databased biomolecular sequence information is a particular advantage of the present invention. Such reagent information identifies genetic information and materials which may be made available to a user of the relational database system of the present invention for further application in research, therapeutic pharmaceutical development or other fields.

This application is primarily directed to the reagent information aspect of the present invention. The reagent information aspect of the present invention is preferably used in conjunction with a biomolecular sequence relational database system, such as the LifeSeq® system developed by Incyte Pharmaceuticals, Inc. Such biomolecular sequence relational database systems are described in U.S. Provisional Patent Application Ser. No. 60/040,033 entitled RELATIONAL DATABASE FOR STORING BIOMOLECULAR SEQUENCE AND REAGENT INFORMATION, filed Mar. 5, 1997, U.S. Provisional Patent Application Ser. No. 60/040,033 entitled BIOMOLECULAR SEQUENCE AND REAGENT INFORMATION RELATIONAL DATABASES AND SYSTEMS, filed Mar. 3, 1998, and U.S. patent application Ser. No. 08/947,845 entitled RELATIONAL DATABASE FOR STORING BIOMOLECULE INFORMATION, filed Oct. 9, 1997, the disclosures of which have previously been herein incorporated by reference for all purposes. Further details regarding database systems with which the reagent information aspect described herein is preferably used may be found in these patent documents.

1. Data Acquisition and Initial Population of the Relational Database

Referring initially to FIG. 1A, a process that may be employed to initially populate relational databases in accordance with this invention is shown. The process begins at a step 6 in which clones from a particular tissue or cell type are sequenced. Specifically, scientists extract mRNA from a sample under consideration (e.g., a particular tissue or cell line) and construct fully complex cDNA libraries. Thereafter, automated sequencing equipment sequences 3000 to 5000 clone templates, for example, from the resulting cDNA library.

The sequences obtained from step 6 provide the initial population of the relational database. The present invention also provides for the selection and further sequencing of certain clones to form a reagent set. This process is described below.

The sequences obtained in step 6 are provided to a bioanalysis system that edits the clone sequences at a step 8 to remove undesirable segments that might interfere with further analysis. The edited result constitutes "useable sequences" 10 of relevance to the database for which sequencing is performed. The useable sequences 10 are ultimately stored in the database.

If mammalian cells are being sequenced, the undesirable segments removed at step 8 may include, for example, mitochondrial and ribosomal DNA, bacterial and lambda phage contamination, nucleotide repeats, and vectors. Of course, some applications may require that one or more of the listed "undesirable" sequences be saved. For example, to study or monitor drug resistance in certain tissue, it may be desirable to record bacterial or viral genome sequences. Regardless of the application, it can be expected that some sequences represent unwanted noise. It is the function of step 8 to remove such noise before further processing.

Next, at a step 12, the bioanalysis system compares the useable sequences against every useable sequence already stored in one or more private internal databases. The comparison produces clustered sequences 14 (sometimes referred to as simply "clusters") which may represent larger continuous nucleic acid sequences comprised of the clone sequence under consideration. Two sequences will be clustered when they meet certain "stringency" requirements based upon their fractional overlap, percent identity, and number of insertions and deletions. A clone sequence having no matches is its own cluster and is commonly referred to as a "singleton."

The bioanalysis system next performs functional analysis on clustered sequences 14, at a step 16, by comparing them against external (e.g., public) gene, protein, and/or pattern databases. Such databases may include "GenBank" for gene and protein sequences and the "Blocks" database for pattern information. GenBank is a public database of sequence information, which is maintained by the National Institutes of Health (NIH). The Blocks database is maintained by the Fred Hutchinson Cancer Research Center in Seattle. It provides functional information about certain commonly occurring sequences (e.g., a sequence associated with kinase activity or ion channel structure).

When the bioanalysis system identifies a match 18 of sufficiently high quality, information regarding the "hit" (i.e., the matching sequence from the public database) is recorded with new sequence at issue. Recorded information includes, for example, the degree of confidence that match is correct, an identifier number uniquely identifying the public database sequence, and keyword/definitional information if available in the public database. This recorded information is referred to collectively as a sequence's "annotation."

If no match of sufficiently high confidence is located against a public database, the cluster under consideration is deemed a "unique" cluster 20. Unique sequences, of course, have no annotation from public databases.

The sequence, cluster, and annotation information provided with useable sequences 10, clusters 14, matches 18, and unique clones 20 are loaded into flat files at a step 22. In a preferred embodiment, each such flat file corresponds to a single table in a relational database.

Finally, the tables populated at step 22 are provided to the end product relational database(s) at a step 24. In a preferred embodiment, the relational database includes a "sequence module" and a "gene expression" module. The sequence module stores unannotated sequences (provided as pure nucleic acid or protein sequences, for example) determined for both the matched and unique clones. The gene expression module identifies the sequences by sequence IDs (without necessarily providing raw sequences) and includes annotated information regarding each of the so identified sequences. In a preferred embodiment, the annotations may be roughly classified as either (1) information about how the sequences relate to one another, and (2) where the sequences originated.

Note that while the process depicted in FIG. 1A shows that clustering step 12 is performed before functional analysis step 16, in one preferred embodiment these two steps are performed in parallel, with a given clone being compared contemporaneously against both other clones in the internal database (step 12) and sequences stored in one or more public databases (step 16).

In a preferred embodiment, raw sequence data (step 6) may be obtained as follows: Messenger RNA (mRNA) is extracted from a sample under consideration (e.g., a particular tissue or cell line) and fully-complex cDNA libraries are constructed. Preferably, these libraries are generated by molecular cloning techniques well known in the art. These techniques make use of the principal flow of expressed genetic information from genomic DNA, to MRNA, to protein. That portion of a genomic DNA sequence which is ultimately expressed as protein is first converted (transcribed) to corresponding (and complementary) mRNA sequences. These mRNA sequences, representing a cell's genes, are extracted from other cellular materials by known techniques, such as affinity chromatography.

A typical cell may contain 10,000 to 30,000 unique mRNA transcripts. For complex tissues (such as brain), this number can be 100,000 or greater. Further, there are three abundance (or prevalence) classes of mRNA; (1) high (super-prevalent) species which exist at greater than 10,000 copies per cell; (2) middle (prevalent) species which exist at 100 to 400 per copies per cell; and (3) low (rare) species which are found at less than 15 unique transcripts per cell.

Clone libraries are composed of complementary DNA (cDNA). Techniques for synthesis of first-strand cDNA from mRNA are well known in the art. One suitable technique is initiated by using (1) a poly-deoxythymidine (poly-dT) primer oligonucleotide that is complementary to the characteristic poly-adenosine (poly-A) tail at the 3' end of most eukaryotic mRNA transcripts; and (2) the reverse transcriptase enzyme. Preferably, the primer used in this reaction also contains a restriction enzyme recognition site (e.g., Not 1) that permits insertion into the appropriate cloning vector. Second-strand cDNA synthesis may employ RNase to nick the mRNA/cDNA hybrid created in the reverse transcription reaction, creating priming cites for *E. coli* DNA polymerase to create second-strand cDNA. The gaps in the second strand may then be ligated together using *E. coli* DNA ligase.

After the ends of the cDNA are blunted with, for example, T4 or Pfu DNA polymerase, an adapter may be ligated onto the end of the double-stranded cDNA. This oligonucleotide, which contains a second enzyme restriction site (usually EcoR1 or Sal1), allows for directional cloning of the cDNA once digestion is complete with the initial restriction enzyme site (e.g., Not1) found at the 3' terminus of the cDNA. The cDNA is then size-fractionated to remove very short cDNAs which would inhibit the ability to generate highly complex libraries. Thereafter, the cDNAs, which, for the most part are complementary sequences of portions of mRNAs which code for proteins, are ligated into a plasmid vector.

Sequencing is an adaptation of the natural process of DNA replication. Therefore, it requires template and primer sequences. One general template preparation and sequencing protocol begins with automated picking of bacterial colonies, each of which contains a separate cDNA clone which will function as a template for the sequencing reaction. The selected colonies are placed into media, and grown overnight. The cDNA templates are then purified from the cells and suspended in water. After DNA quantification, high-throughput sequencing is performed using sequencers, such as Applied Biosystems, Inc., Prism 377 DNA sequencers, followed by analysis and lane retracking. These "first pass," or "high-throughput" sequences are generally a partial sequence of their associated clone, starting from the 5' end of the clone. They are unique identifiers of their respective clones, and are sometimes referred to as expressed sequence tags (ESTs). As mentioned, an EST is generally about 50–300 nucleotides in length and, depending on cloning and sequencing strategy, may cover all, but more frequently a fraction, of the gene sequence. The cDNA clones from which ESTs are derived are generally part of libraries, each of which represents a collection of genomic information expressed for a given tissue or sample. Typically, libraries containing more than 1 million clones are generated.

Sequences obtained via other methods are, or course, also useful. In fact, any nucleic acid or peptide sequence data obtained from biological samples may be employed in the relational databases/processes described herein.

Raw sequences are extracted from sequence template files and either (1) cleaned up and passed on for further analysis; or (2) removed because no useful sequence remains. This process is accomplished at step 8 of FIG. 1A. In one embodiment, an edited sequence must have at least 50 bases to continue beyond the sequence editing step.

In a preferred embodiment, step involves first clipping recognized 5' and 3' vector sequences using dynamic programming. Then regular expression matching to 5' PolyA (or 3' PolyT) patterns is used to clip the mRNA tail. The remaining sequence is checked for sequencing artifacts using, for example, Nearest Neighbor analysis.

Next, a series of BLAST comparisons is done to clean up the sequence. Low-information segments (e.g., dinucleotide repeats) are masked-replaced by Ns to prevent subsequent spurious matches. Sections containing recognized contamination (e.g., vector) are removed. Dispersed repetitive elements (e.g., Alu, LINE, MIR) are masked. Finally, recognized mitochondrial and ribosomal RNA sequences are removed.

Before entering the functional analysis block (which performs step 16), new sequences are compared against existing clone sequences stored in an internal database (e.g., an Incyte Pharmaceuticals, Inc. LifeSeq® relational database) at step 12; this step is the basis for the cluster assignments. Preferred clustering techniques will be discussed in detail below. For now, it should be recognized that the clustering process looks for overlap between terminal sequences of clones (1) to construct longer sequences (clusters) composed of the individual overlapping clones, and (2) to classify new clones as belonging to a known sequence already provided in the internal database. As the EST clones described herein are rather short (e.g., 50–300 base pairs), they do not represent full length mRNA. Therefore, their information content can be increased when they are clustered.

As noted, functional analysis (step 16) annotates sequences based on their similarity to identified sequences in public databases. Exact matches as well as homologies are detected and recorded. If no sequence similarities are found, a sequence is evaluated for patterns indicating functional motifs. In one embodiment, matching between new sequences and public database sequences employs the same technique used to cluster clones (step 12).

In a preferred embodiment, functional analysis (step 16) involves a series searches that compare the new sequences against already-identified sequences in external databases. In GenBank, the searches may be conducted in the following order:

1. GenBank Primate DNA sequences
2. GenBank Rodent DNA sequences
3. GenBank Primate Protein sequences
4. GenBank Rodent Protein sequences
5. GenBank Mammal Protein sequences
6. GenBank Vertebrate Protein sequences
7. GenBank Eukaryote Protein sequences In GenBank, all sequences are assigned an arbitrary GenBank Identifier number ("GI"), which serves as a unique tag for that sequence. If an internal gene expression database sequence matches a GenBank entry, it is annotated with one of these GI numbers, depending on whether the match was to the nucleotide or protein sequence of the GenBank entry.

In a preferred embodiment, each matched internal sequence includes a Description field which is annotated with data from the Definition field (nucleotides) and/or Keyword field (proteins) of the Entrez Document Report (Entrez, like GenBank, is part of the National Center for Biotechnology Information, or NCBI). To optimize text searches of gene expression database entries, these fields may be screened prior to annotation to remove redundant words and standardize nomenclature. This means that, for a protein sequence, the Description field may be blank if the GenBank protein description had low information content (for example, "induced protein").

Figure 1B:
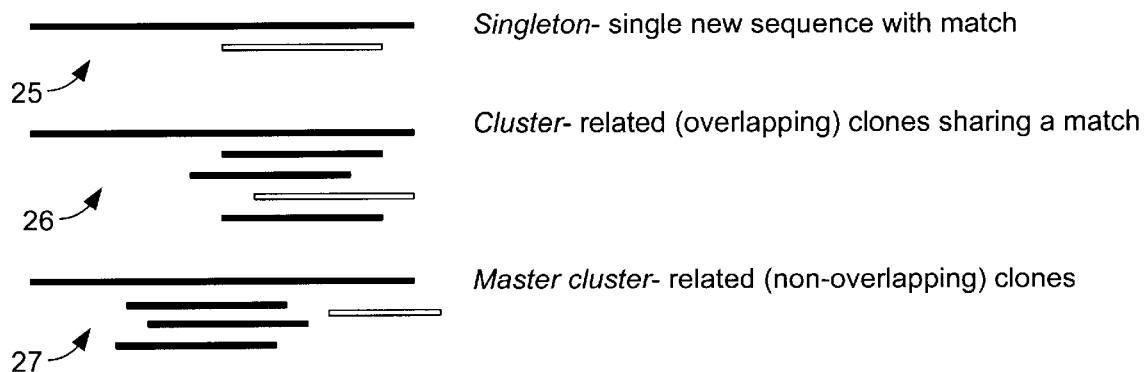
FIG. 1B is an illustration of various categories of sequence clusters and public database matches that may be identified in the relational databases of this invention.
Figure 1B:
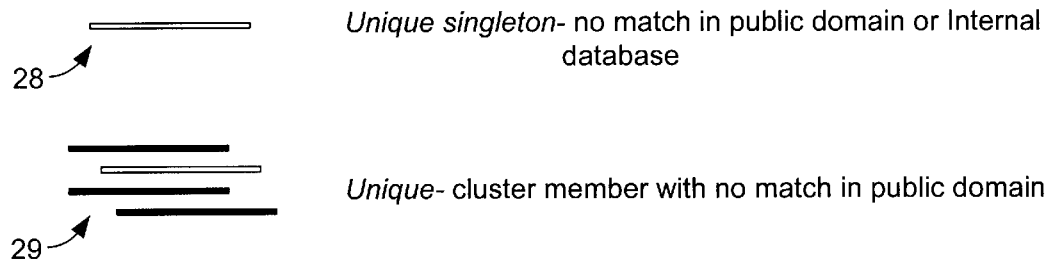

Some of the possible clusters and public database matches are illustrated in FIG. 1B. The top three examples of the figure show how new sequences (represented as light horizontal bands) may be matched with public database sequences (represented by long dark horizontal bands). In example 25, a "singleton" (unclustered clone sequence) matches a public-domain gene. In example 26, a "cluster" of clone sequences matches a public-domain gene. And in example 27, both a cluster and a singleton match the same public-domain gene to form a "master-cluster." The term master-cluster also refers to two or more clusters matching the same public-domain gene. The bottom two examples show how unique sequences (new sequences that have no current match in a searched public database) may be grouped. Group 28 is a group of one clone or a "unique singleton." Group 29 is a unique cluster of multiple clones, none of which matches a current searched public database sequence.

A number of computer platforms can be used to perform the necessary calculations for various processes of the present invention. For example, a number of computer workstations from a variety of manufacturers can be used to perform the steps 8, 12, and 16 of FIG. 1A. In particular, workstations manufactured by Silicon Graphics, Inc. (SGI) and multiprocessor (e.g. 4 processor) Alpha Systems manufactured by Digital Electronics Corporation (DEC) have been found to be suitable for performing such calculations.

2. Nomination of Clones for a Reagent Set

As noted above, in one aspect, the invention provides a set of reagents. As used herein, a reagent is a clone which has been selected from a library or libraries of clones based on criteria designed to identify clones which are good candidates for further research. A reagent clone has been resequenced and verified so that, for example, it may be provided to third parties for further research. A reagent may be used, for example, to do additional sequencing on the clone insert; the clone may be placed in an expression vector to make its associated protein; the clone's expression may be monitored, for example, using a biological microarray or northern blot technique; the reagent may be used to identify (pull out) additional related clones; or a set of reagent clones may be used as hybridizable elements on a biological microarray. In accordance with the present invention, data relating to reagent information may be stored in a relational database, preferably as an add-on to a broader biomolecule relational database, for example, a database of ESTs, such as Incyte Pharmaceuticals, Inc.'s LifeSeq® database. In a particularly preferred embodiment, clones are "nominated" for inclusion in a reagent set from relational database of biomolecule sequence information, which is then supplemented with the additional reagent information. Procedures for selecting and databasing such a reagent set in accordance with preferred embodiments of the present invention follow.

The invention provides a method for selecting clones for a reagent set according to a set of specified criteria. The process comprises "nomination", the initial tentative selection of a clone, and "verification", confirmation of the quality of the clone insofar as its ability to be propagated in the laboratory, and resequencing to verify that its initial sequence is correct. If a clone is nominated but fails to be verified, the nomination steps may be repeated to identify an alternate clone. The target reagent set is one that contains a representative clone for every gene in a genome. In a particularly preferred embodiment, the target reagent set is one that contains a representative clone for every gene in the human genome.

In a preferred embodiment of the nomination procedure, the pool from which candidate clones are selected is identified by sequence tags (e.g., ESTs) in a relational gene expression database, such as Incyte Pharmaceuticals' Inc.'s LifeSeq® database. Reference will be made to Incyte's LifeSeq® database and system in the description of the preferred embodiment of the present invention which follows. Further details regarding such databases may be found in Provisional Patent Application Ser. Nos. 60/040,033 and 60/040,033 and patent application Ser. No. 08/947,845 previously incorporated by reference herein. Clones may be selected en masse by software designed to pick clones for maximum coverage (e.g., at least one clone per known or putative gene). Alternately, clones may be nominated using methods that target related genes with a particular function. Nomination is an ongoing process, with clones being nominated for newly discovered master clusters as well as alternates for any genes whose previous nominee failed, as described in more detail below.

The principal en masse nomination mechanism selects one or more candidate clones for every LifeSeq® Master Cluster. Clusters refer to a group of polynucleotide EST sequences that overlap with each other, with high enough match quality as indicated by a product score of 50 or greater. Clustering is transitive, such that if sequence A clusters with sequence B, and B clusters with C, A and C are considered members of the same cluster. A Master Cluster is a group of clusters that share the same "GenBankHit" (most similar sequence found by comparing to the GenBank database) even though the sequences from one component cluster do not match those from the other clusters with the requisite product score. A singleton is an EST that does not cluster with other ESTs. It may be unique, lacking a GenBank hit, or it may be non-unique if it is similar to a sequence in GenBank. A master cluster is a representation of a putative gene.

Nomination of representative clones from non-singleton master clusters is based on several criteria to pick one or more appropriate candidates from the multiple clones available. As noted above, a principal goal in building a reagent information database in accordance with the present invention is to have a representative clone for every gene in a given genome of interest (e.g., the human genome). The target is complete coverage. Therefore, the nomination process is designed to identify and provide as a reagents these clones which are most likely to contain the complete gene sequence. The 5'-most clone is usually preferred because it is most likely the longest, and the one most likely to contain the complete gene. However, there is also a preference for clones in the vector pINCY (a vector prepared by removing the EcoR1 restriction site in pSPORT, and cutting the HindIII site and creating a new EcoR1 site in its place; the resulting plasmid cuts with EcoR1 and Not1, but not HindIII) such that a shorter clone in pINCY may be selected if the longest clone is in another vector, and the pINCY clone is no more than 150 nucleotides shorter than the longest clone. If two equivalent clones are available, the one most recently analyzed (initial sequence (e.g., EST) obtained for the clone's polynucleotide insert; for LifeSeq®, the one with the highest clone number) is selected.

To carry out nomination of master clusters based on the criteria above, a multi-step process is used. In the first step, the set A of non-singleton master clusters in the most recent version of LifeSeq® are identified using a combination of SQL queries and perl (Practical Extraction and Report Language) scripts; a perl script is also used to determine the set B of master clusters corresponding to clones already in the reagent set. Those master clusters in set A but not in set B comprise the list of master clusters to be examined for nominees.

Once this list is obtained, the second step is to collect the initial sequences (ESTs) of each master cluster for assembly. In a preferred embodiment, a perl script is used to collect the sequences, by querying LifeSeq® to determine all the clusters within a given master cluster, then the clones comprising those clusters, and finally the IDs of the sequences for those clones. In addition, the ID of any GenBank hit is also recorded. The script uses these sequence IDs to retrieve the actual nucleotide sequences of the ESTs and GenBank hits, writing them into a FASTA-format file in a directory corresponding to that master cluster. The script then performs the same operations for each of the remaining master clusters until a directory with a FASTA sequence file for every master cluster has been created.

The third step is to create a multiple sequence alignment (an assembly) for each of the master clusters, using the sequences in the FASTA file created by the previous step. The "phrap" assembly program, developed by Phil Green of the University of Washington, uses the Smith-Waterman alignment algorithm and can be used to create these assemblies. A perl script is used to manage the task of running phrap on each of the master cluster sequence files, simultaneously running a predetermined number of phrap jobs at all times, to take advantage of resources on multi-processor machines, in this computationally intensive step. The output of phrap is an ".ace" file that describes the alignment(s) produced from the input sequences. An ace file might contain more than one "contig" (contiguous assembly of sequences) if the input sequences represent multiple genes or perhaps different splice variants of the same gene.

The final step in master cluster-based nomination is to examine the .ace file for each master cluster, and to nominate clones based on their 5' position in a contig (master clusters with multiple contigs may have more than one nominee) as well as vector criteria. A perl script is used to read each of the ace files, apply the nomination criteria, and write the clone and corresponding master cluster to a file summarizing the results for the entire set of master clusters (the "nomination file"). The list of clones from this file is sent to the lab for retrieval from stock cultures, resequencing, and verification, described below.

Nomination of clones for singleton master clusters is a simpler process, since only one clone per master cluster exists. Lists of these clones can be retrieved directly from LifeSeq® by SQL queries or perl scripts. Additional criteria may be used to insure quality. For non-unique singletons, a product score cutoff may be applied, so that, for example, only clones with a Product Score of 40 or greater are selected. Alternately, the GenBank hit may be taken into consideration, so that non-unique singletons whose product score is less than 40 may still be nominated provided that no other representative clone for that GenBank sequence already exists in the reagent set. For unique singletons, there is no GenBank hit with which Product Score or hit identity criteria can be applied. For these, clones may be nominated from libraries enriched for rare transcripts by normalization (e.g., Soares normalization) or subtraction processes well known to those of skill in the art. Singletons from these libraries are considered more likely to represent a genuine unique, novel gene (rather than merely a poor quality sequence) than similar clones from standard libraries.

Clones may also be nominated with algorithms that target particular gene families of interest. For example, clones can be nominated by using motif search algorithms, such as by identifying those sequences containing a signal peptide by using Hidden Markov Models (HMMs), as described more fully in Eddy, S. R., *Hidden Markov Models*, Current Opinions in Structural Biology (1996) 6:361–365, which is incorporated herein by reference for all purposes. HMMs can be used to find shared motifs, specifically consensus sequences. HMMs have a formal probabilistic basis and use position-specific scores for amino acids or nucleotides. The algorithms are flexible in that they incorporate information from newly identified sequences to build even more successful patterns. Further, clones can be nominated using homology search algorithms, such as BLAST, by gene prediction algorithms, such as Genemark, Grail, and Genefinder, and by algorithms that convert a multiple alignment of peptide sequences into a scoring matrix for comparison to a query nucleotide sequence, such as BLIMPS, and the like.

Once a clone has been nominated for the reagent set based on the foregoing criteria, the quality of that clone is preferably verified by confirming that the clone is viable and can grown to amounts suitable for isolating the clone insert sequence. Nominated and verified clones are then subjected to further sequencing. This resequencing involves the extension of an initial sequenced portion of a clone of a gene of interest (e.g., an EST) by a variety of methods which use conventional molecular biological techniques and recently developed adaptations of these techniques. Techniques which may be used for such further sequencing of initial sequenced portion of a clone (e.g., ESTs), including 5' and 3' long read sequencing, are described in U.S. patent application Ser. No. 08/811,758 entitled PROJECT-BASED FULL-LENGTH BIOMOLECULAR SEQUENCE DATABASE, filed Mar. 6, 1997, the disclosure of which is incorporated by reference herein for all purposes in particular with reference to FIG. 1B of that application.

After resequencing, the 5' and 3' long read sequences may be screened using a protocol similar to the standard LifeSeq® Block I protocol, which trims vector and linker sequences, masks repetitive element and low information regions, and removes clones containing bacterial, mitochondrial, or ribosomal sequences. Clones that are removed in this screening are not considered further for inclusion in the reagent set. Then, the 5' long read sequence is compared with the initial 5' short read (e.g., EST) sequence of the same clone. In this preferred embodiment, this comparison is done using the program "lalign", which (like phrap) implements a Smith-Waterman algorithm. The resulting alignment is examined to determine if the sequence passes or fails, based on a set of criteria, such as: The 5' long read sequence must overlap the short read sequence by at least 50 bases, and be 40% identical with the short read or it is automatically failed. Overlaps greater than 100 bases long and 90% identical or better, and those 50–100 bases long and 95% identical are automatically passed. The remaining alignments (those with between 40–90% identity) are manually inspected to determine whether the clone should pass or fail, based on the precise amount of identity and the overall quality of the long read sequence. Threshold values for passage or failure may be set by a user. Those clones which pass this final step are considered verified and are made part of the reagent set.

In a preferred embodiment, clones undergoing resequencing for verification are processed in groups ("lots") of 96 clones, one for each chamber of a 96-well plastic culture dish (each chamber/well is an indentation in the dish that can hold a liquid such as a bacterial culture separate from all the others). After verification, clones that "pass" are re-racked (transferred) into new lots for storage. When reagent clones and associated data are provided to third parties, such as customers purchasing the clones for further research, the reagent clones are preferably shipped in these lots. A customer receiving clones and their sequences must know not only that the clone has been received, but also its precise location, if s/he is to make use of the reagent. Lot and Well information is recorded for each reagent clone that passes the post-nomination processing to tell the customer where to find the clone. (EG clone 1234567 is located in lot #14332, well #G03).

Data accumulated in resequencing and processing of reagent clones (also referred to herein as reagent specifications) are loaded into flat files which are ultimately loaded into the end product reagent information relational database.

Figure 1C:
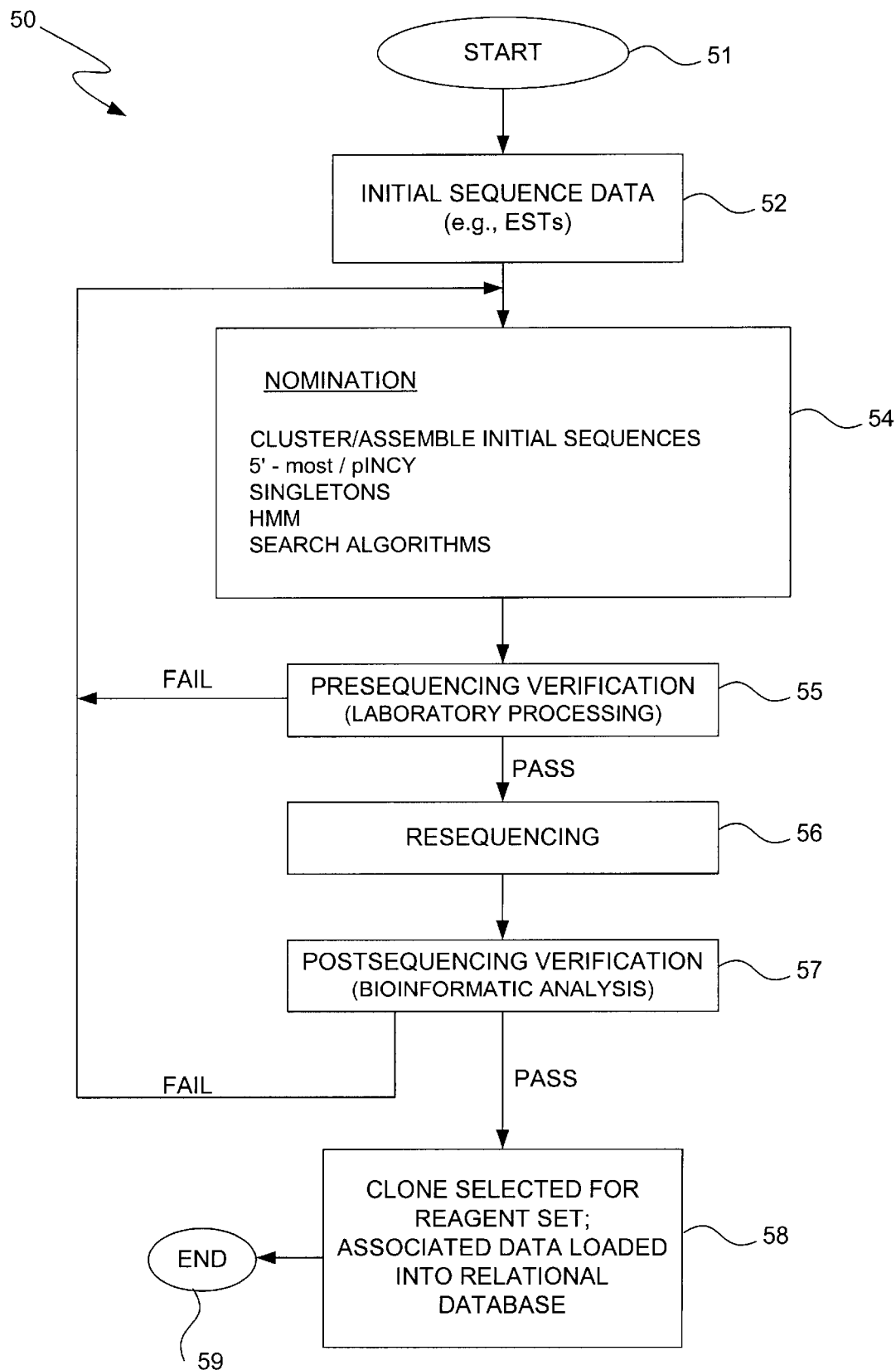
FIG. 1C is a flow diagram presenting key steps employed to nominate clones for a reagent set in accordance with one embodiment of the present invention.

FIG. 1C provides a process flow for the generalized process of creating a reagent set in accordance with a preferred embodiment of the present invention. Process flow 50 begins at 51 and at a step 52 primary sequence data relating to set of clones is provided. In a preferred embodiment this primary sequence data is EST data stored in a relational format, such as in the LifeSeq® database system of Incyte Pharmaceuticals, Inc. As described above, these ESTs, each of which corresponds to a single clone, are analyzed in computer-based nomination system at a step 54 to identify a subset of clones which are most likely to contain complete gene sequences. Nominated clones are then subjected to laboratory processing to verify that the clone is viable and can grow to amounts suitable for isolating the clone insert sequence at a step 55. Nominated clones passing this verification screening are resequenced at a step 56. Then, at a step 57, a second, bioinformatic verification screening is performed to ensure purity and that the nominated clone's initial sequence and the 5' long read sequence obtained in resequencing are from the same clone. If a nominated clone fails either verification screening, it is discarded and another clone is nominated according to the same procedure. If the clone passes all of the processing tests, it is selected for the reagent set at a step 58, and its associated data is loaded into the relational database. The process ends at a step 59.

3. The Database Environment

Figure 2A:
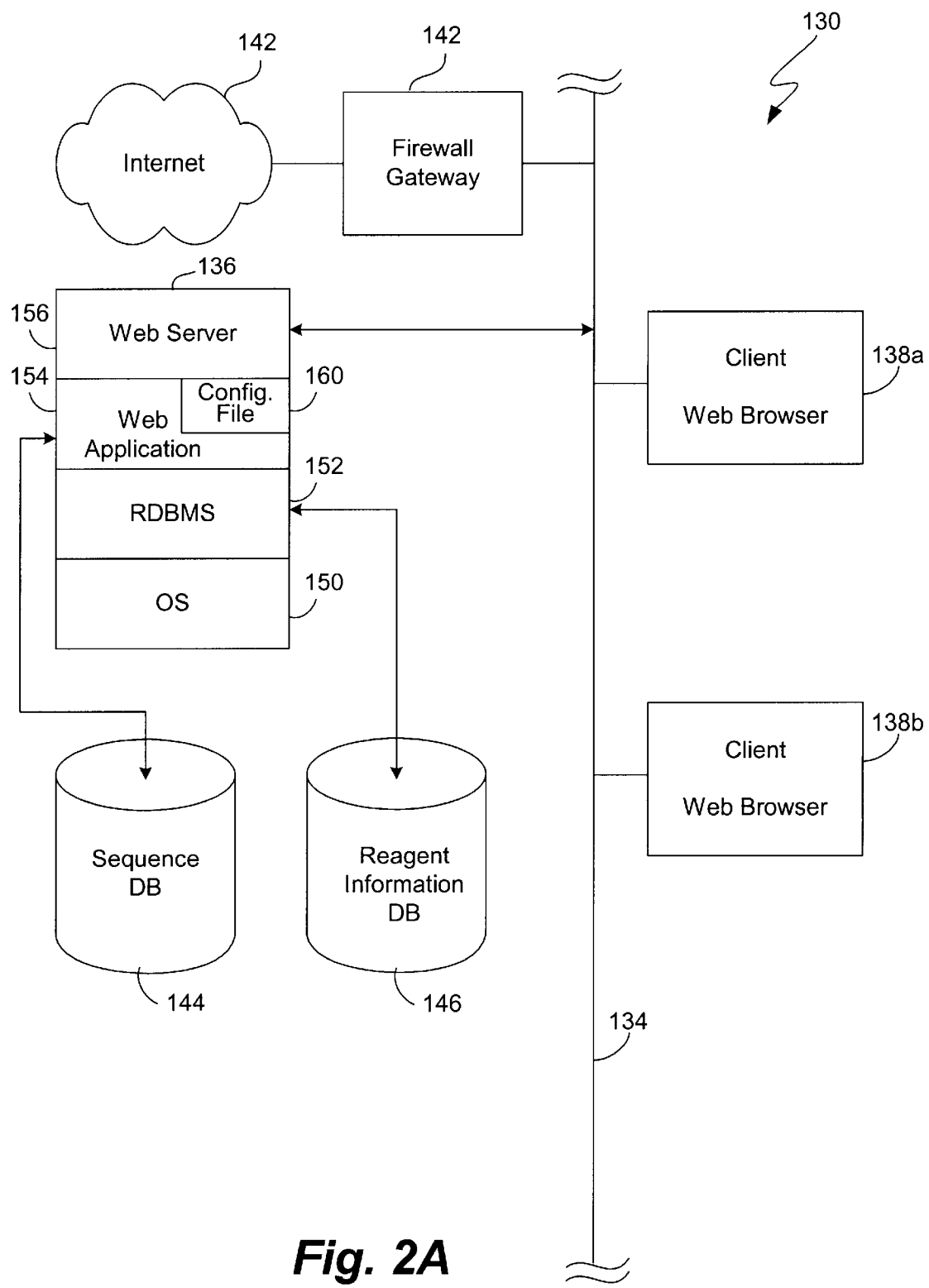
FIG. 2A is a block diagram of a client-server Intranet for providing database services in accordance with one embodiment of the present invention.

FIG. 2A depicts a network system 130 suitable for storing and retrieving information in relational databases of the present invention. Network 130 includes a network cable 134 to which a network server 136 and clients 138a and 138b (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138a and 138b. In a preferred embodiment, depicted in FIG. 2A, the software running on the server machine supports the World Wide Web protocol for providing page data between a server and client.

Client/server environments, database servers, and networks are well documented in the technical, trade, and patent literature. For a discussion of database servers and client/server environments generally, and SQL servers particularly, see, e.g., Nath, a., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., SQL statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138a and 138b includes a World Wide Web browser for providing a user interface to server 136. Through the Web browser, clients 138a and 138b construct search requests for retrieving data from a sequence database 144 and/or a reagent information database 146. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or reagent information database 146.

In the embodiment shown, the Web application accesses data in reagent information database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

Figure 2B:
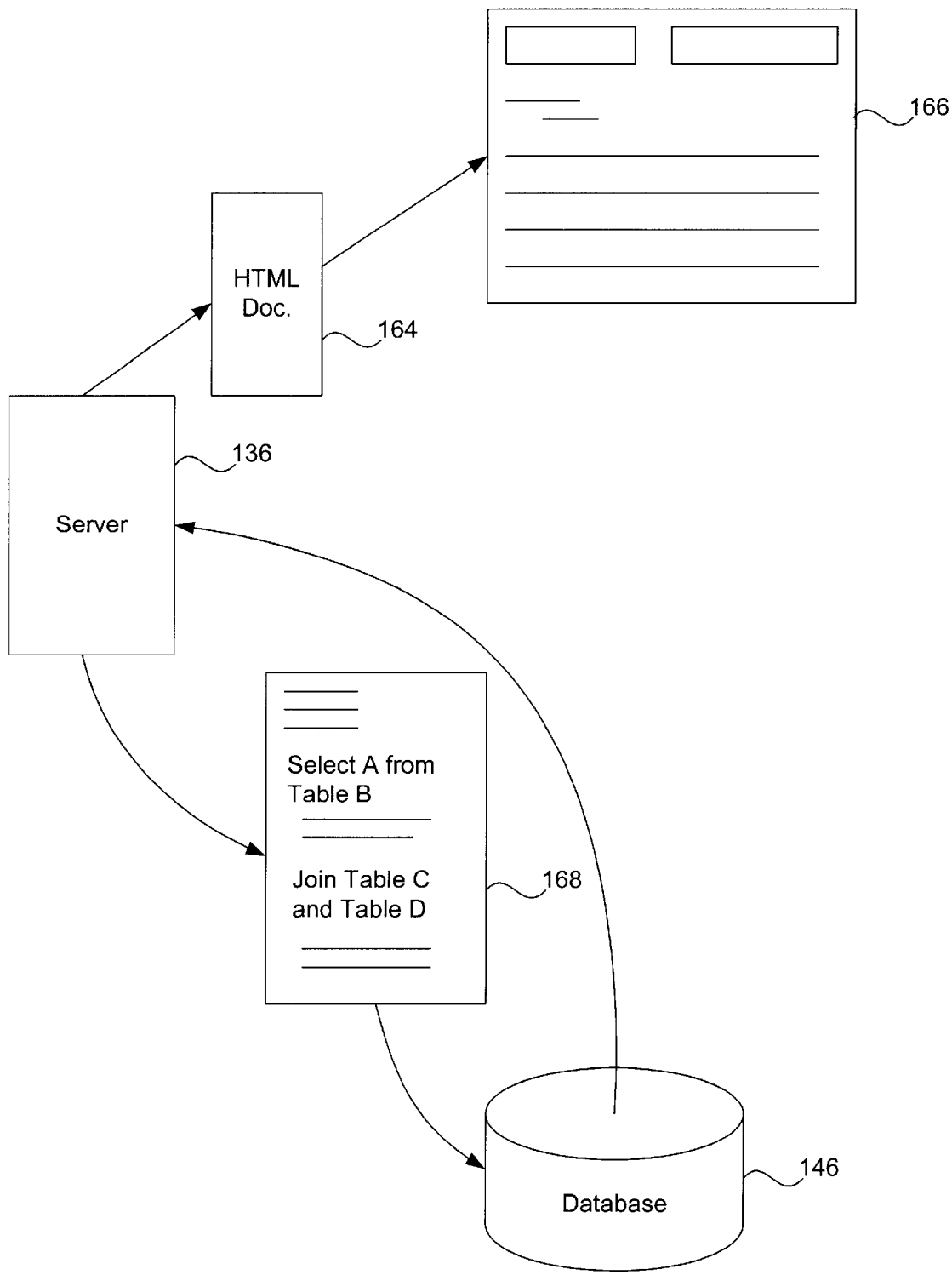
FIG. 2B is a schematic representation of the various software documents entities employed by the FIG. 2A client-server Intranet to provide biological information in response to some user queries.

The procedure by which user requests are serviced is further illustrated with reference to FIG. 2B. In this embodiment, the World Wide Web server component of server 136 provides Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document relaying the database information to the client as a view in user interface 166.

While the embodiment shown in FIG. 2A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

It should be noted that if the contents of the local databases are to remain private, a firewall 140 must preserve in confidence the contents of a sequence database 144 and a reagent information database 146.

In a preferred embodiment, the reagent information and sequence databases include a plurality of tables containing information about ESTs which as noted above are short sequences (about 50–300 base pairs) of cDNA transcribed from mRNA. As noted, these EST sequences may be used in the reagent clone nomination process for a reagent set which may then be used to supplement such an EST database. An example of an EST (gene expression) database is the LifeSeq® database available from Incyte Pharmaceuticals, Inc. and described in Provisional Patent Application Ser. Nos. 60/040,033 and 60/040,033 and patent application Ser. No. 08/947,845 previously incorporated by reference herein.

In a preferred embodiment, sequence database 144 is a flat file database including separate partitions for different types of data. If it contains other information such as EST sequences, these may provided in a separate partition. Other approaches include partitioning the sequence data according to species such as human, primate, rodent, etc. Still further, separate partitions may be provided for sequences that have been found to be unique to the local database (i.e., sequences that did not have any hits in an external database such as GenBank).

Preferably, the information in reagent information database 146 is stored in a relational format. As mentioned, it may include tables for both EST and reagent information. In Oracle™ databases, for example, the various tables are not physically separated, as there is one instance of work space with different ownership specified for different tables. In Sybase™ databases, in contrast, the tables for the reagent information and the table for ESTs may be physically segregated into different "databases."

One specific configuration for network 130 for multiple users provides both the reagent information and sequence databases on the same machine. If there is a high volume of sequence searching, it may be desirable to have a second processor of similar size and split the application across the two machines to improve response time.

A suitable dual processor server machine may be any of the following workstations: Sun-Ultra-Sparc 2™ (Sun Microsystems, Inc. of Mountain View, Calif.), SGI-Challenge L™ (Silicon Graphics, Inc. of Mountain View, Calif.), and DEC-2100A™ (Digital Electronics Corporation of Maynard, Mass.). Multiprocessor systems (minimum of 4 processors to start) may include the following: Sun-Ultra Sparc Enterprise 4000™, SGI-Challenge XL™, and DEC-8400™. Preferably, the server machine is configured for network 130 and supports TCP/IP protocol.

Depending upon the workstation employed, the operating system may be, for example, one of the following: Sun-Sun OS 5.5 (Solaris 2 5), SGI-IRIX 5 3 (or later), or DEC-Digital UNIX 3 2D (or later).

The databases of this invention may be downloaded via a 4×4 Gb+ FWSCSI-2, Fiber Link Raid Units 2OGb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape Web Browser.

The network may include a 10-base-T connection, be TCP/IP capable, and provide access to Internet for HTML hyperlinks to NCBI.

4. Model of the Reagent Information Relational Database

Figure 3:
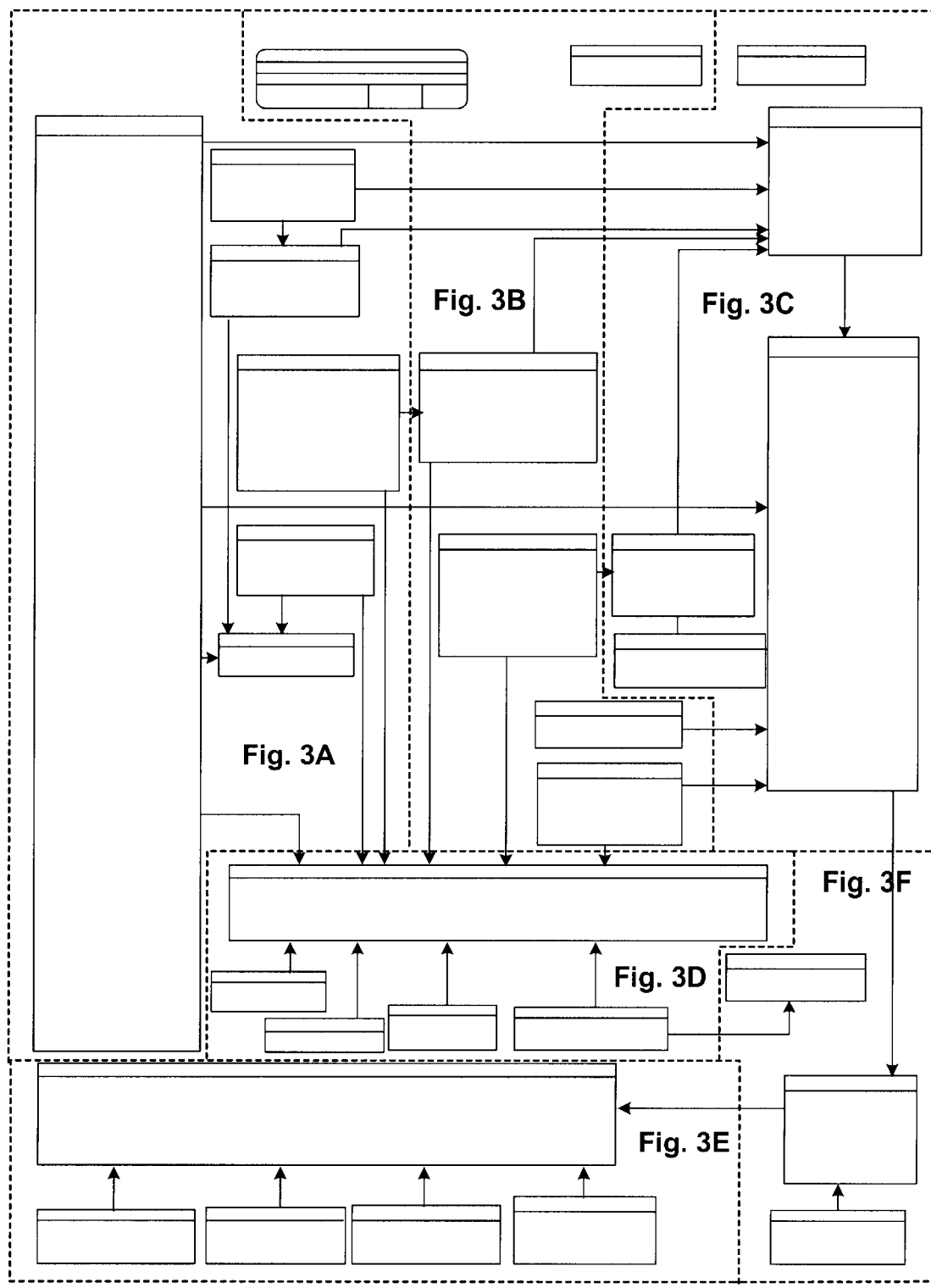
FIG. 3 is a physical data model for a reagent information relational database in accordance with a preferred embodiment of the present invention.
Figure 3A:
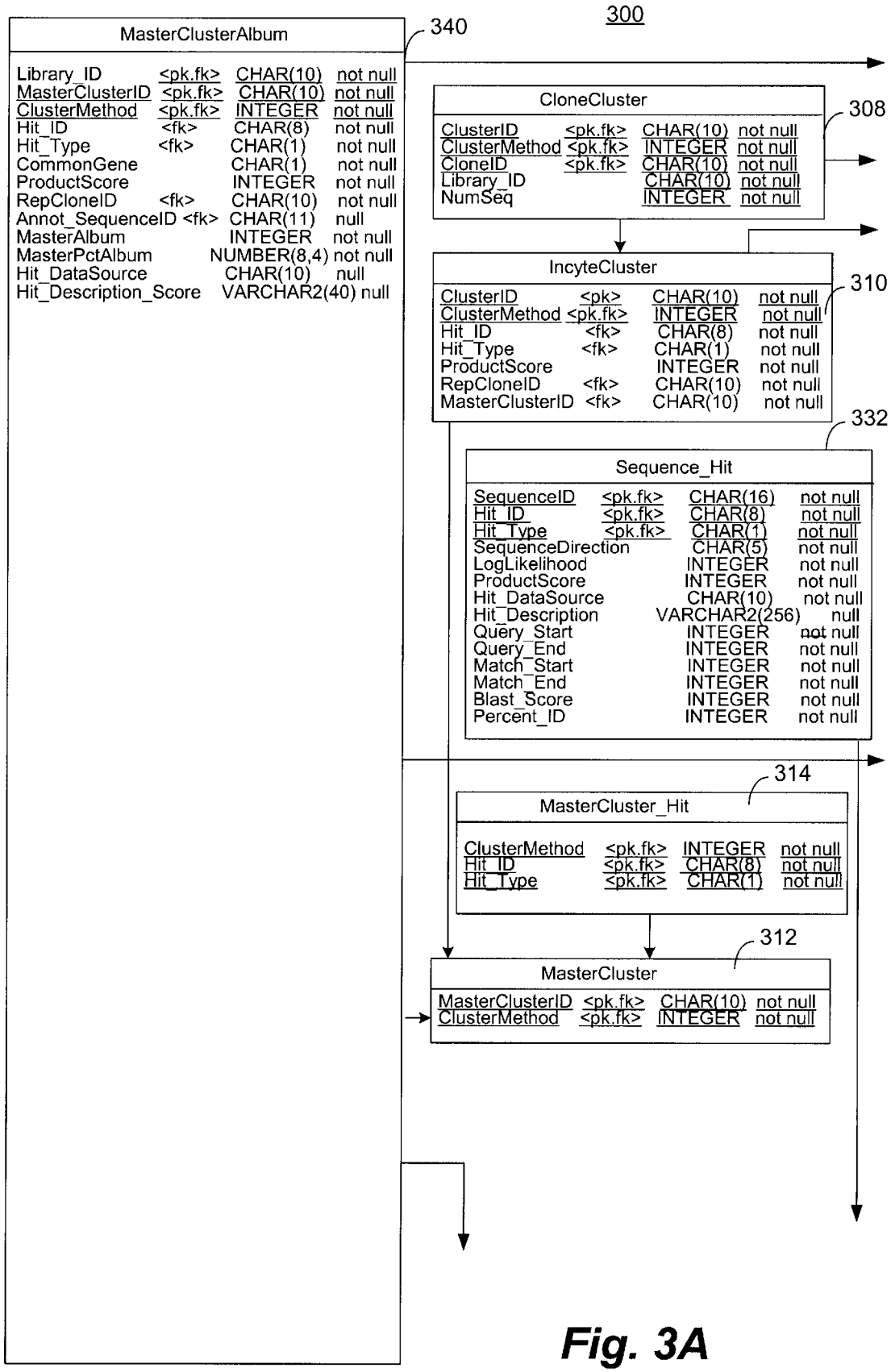
Figure 3B:
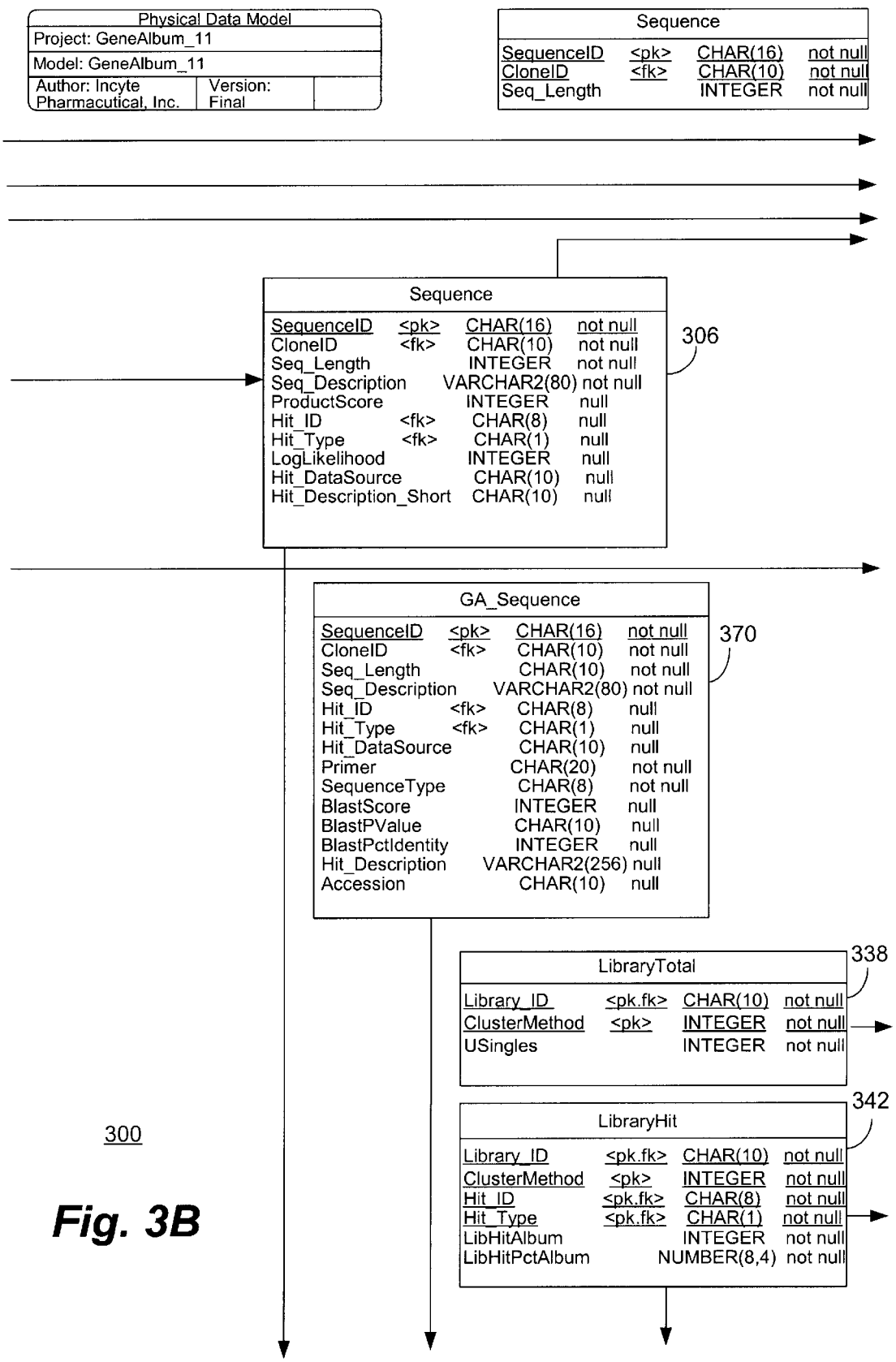
Figure 3D:
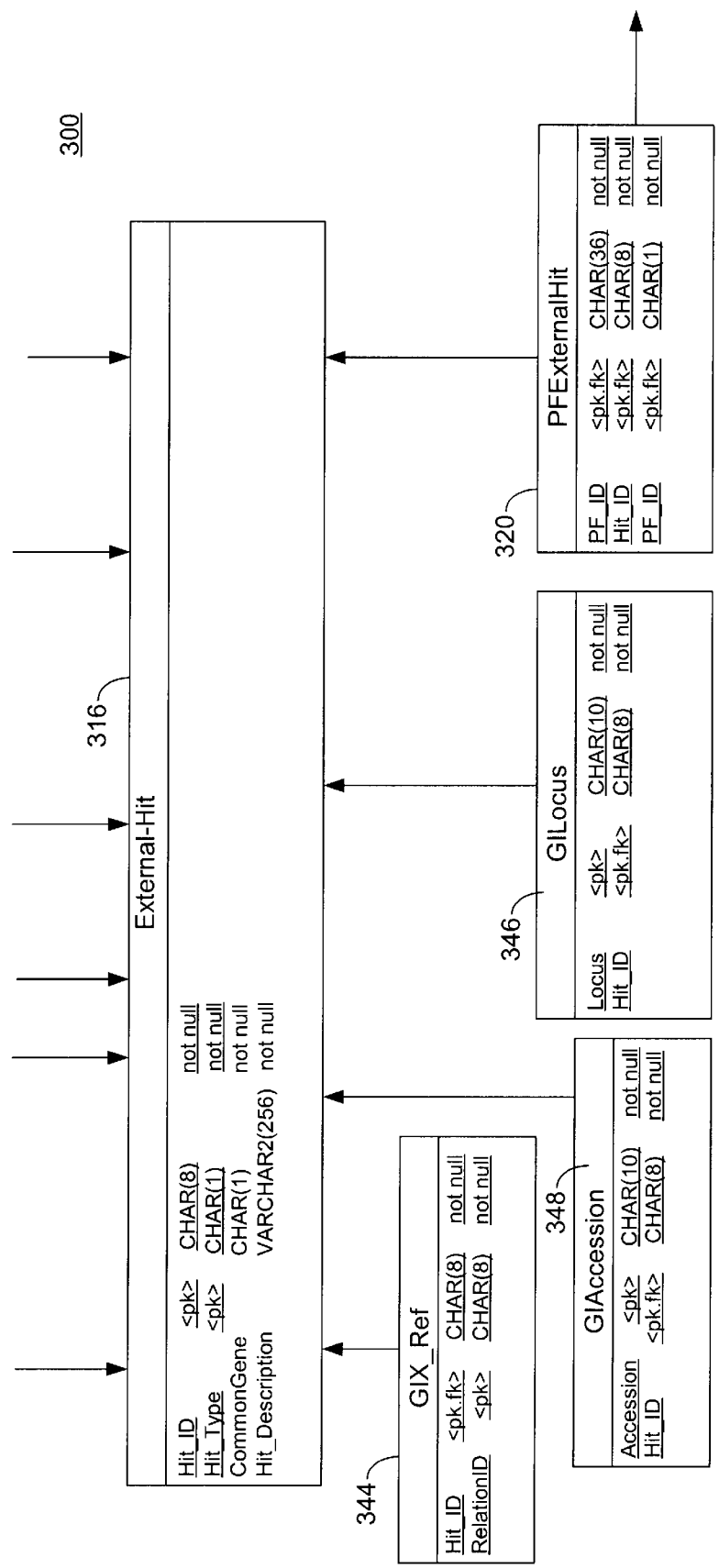
Figure 3E:
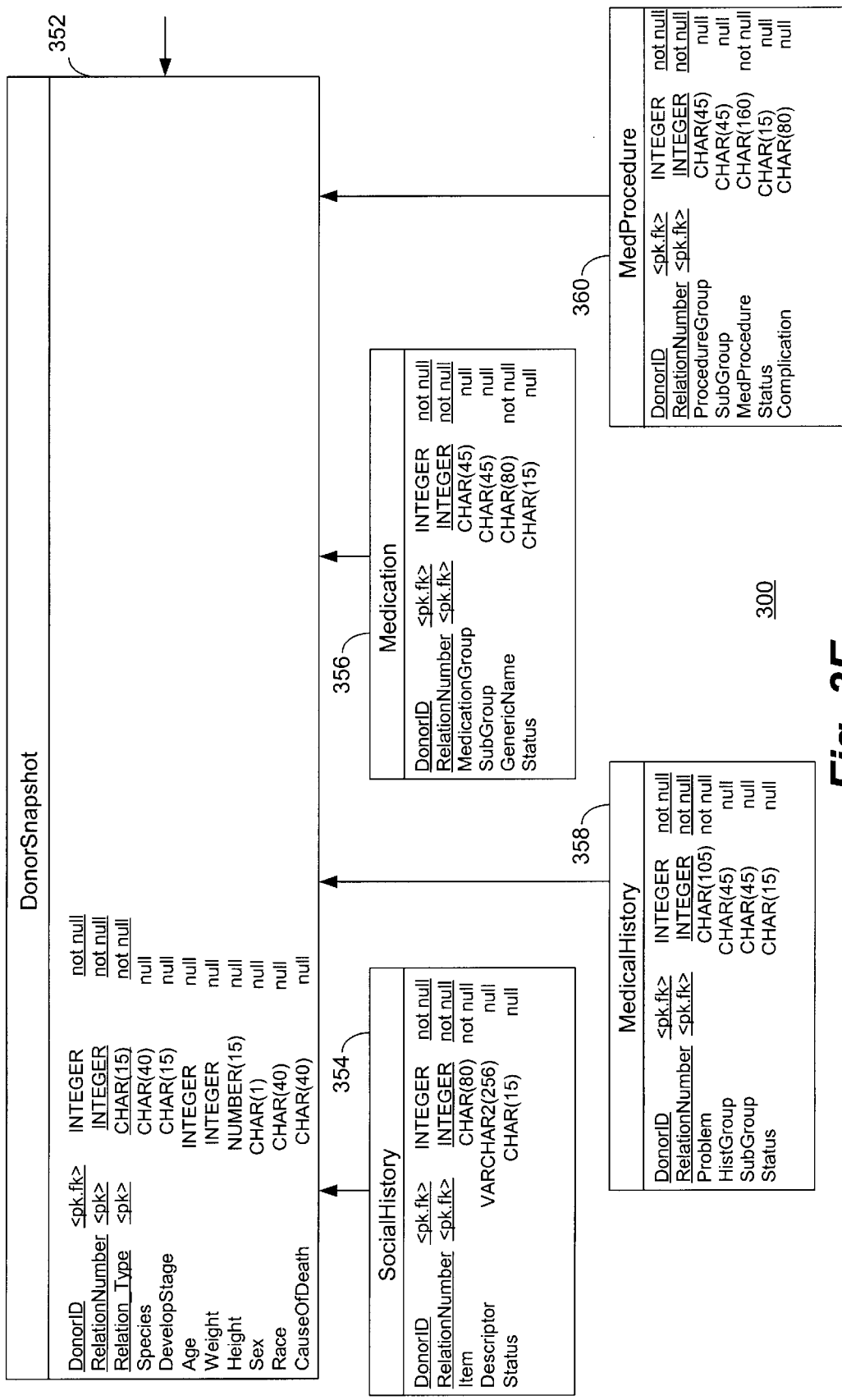
Figure 3F:
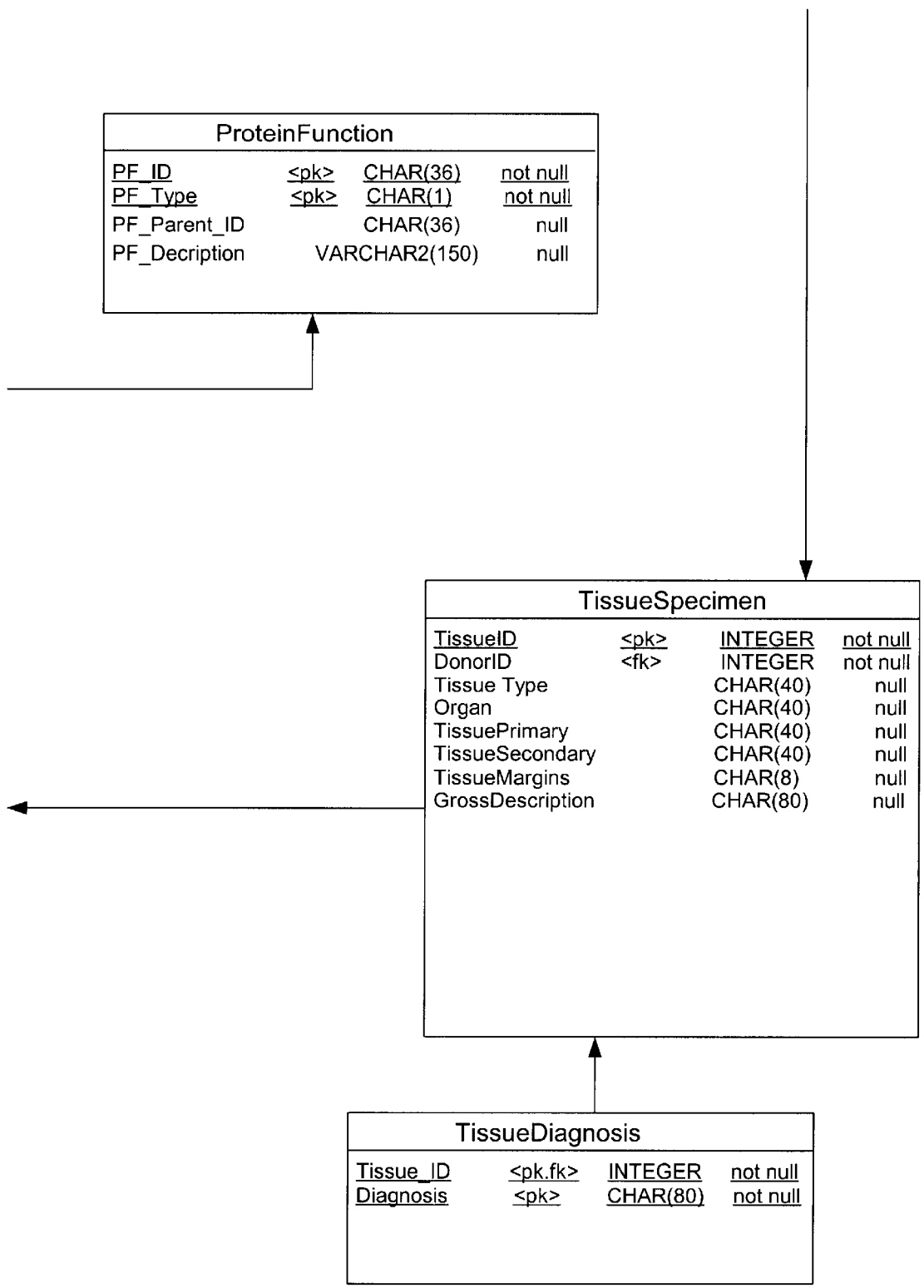

Turning now to FIG. 3, a block diagram is shown of a physical data model for a reagent information relational database 146 in accordance with one embodiment of the present invention. The physical data model 300 represents the actual physical locations of various records within the tables of the relational database 146. Each block represents a separate table provided in the database composed of records. A physical database model table may be uniquely identified by one or more records known as a "primary key". Primary keys are identified by underlining and by the designation "pk". A physical database model table may also contain a field or fields which are already defined in one or more other tables in the database. Such fields are known as "foreign keys" and are designated by a "fk" in the physical data model 300. The foreign key information is included in the physical data model 300, since it is useful for a full understanding of how the database is organized and how the data is related and accessed. The physical data model 300 includes arrows between the tables representing the relationship of the foreign key (or keys) in a table to another table for which the foreign key(s) is a primary key.

As noted above, the present invention is preferably an add-on to a relational sequence database, such as a gene expression database, for example Incyte's LifeSeq® database. Thus, the preferred data model for the reagent information relational database, shown in FIG. 3, includes tables for the information contained in such a gene expression database and adds additional tables and fields for data particularly related to the reagent information aspect of the present invention.

A Library table 302 includes a record of each library in the gene expression database. As noted, such libraries are generated from a single tissue or other biological sample. The attributes of records in Library table 302 include a "LibraryID" (primary key) and a number "usable" sequences (i.e., clones remaining in the library after sequence editing at step 8 of FIG. 1A) in the library. In addition, table 302 provides a "TissueID" attribute (foreign key inherited from a "TissueSpecimen" table 330) and a "Tissue_Category" attribute. Some possible tissue categories include cardiovascular, dermatological, developmental, endocrine, gastrointestinal, hematopoietic/immune, hepatic, musculoskeletal, nervous, pancreatic, male reproductive, female reproductive, respiratory, sensory, and urologic. The TissueID provides a connection to a collection of six tables (including tissue specimen table 330) which tie in biological details of the tissue's donor. These tables will be described in more detail below. Still further, library table 302 includes "Lib_Description" and "Lib_Comment" attributes which may provide short and long, respectively, descriptive information about the library such as preparation techniques and related gene expression libraries. Preferably, the Lib_Description attribute follows a standard format such as: tissue name, disease state, patient age/gender, special information. For example, an entry might read:

colon, Crohn's, 40 M, match to COLNNOT05

Each library in Library table 302 has associated "library total" records which are stored in a "LibraryTotal" table 338. These records provide the number of unique singletons "USingles" found in the specified library (Library ID) for a given cluster method "ClusterMethod." The cluster method refers to the stringency of the match employed to form the cluster (e.g., a stringency with a Product Score of 50 or 70 as described see below) or any alternative clustering technique. This information gives the user some indication of how many unique sequences appear in the library, and how many are matched to public-domain sequences.

Each record in Library table 302 may reference multiple clones which are described in a Clone table 304. The records of Clone table 304 include specifics of sequenced clones from each library, including a "CloneID" (primary key); a Library_ID (foreign key inherited from Library table 302); a "NumSeqs" which specifies the number of sequences available for each clone; an "Annot_SequenceID" which identifies the Sequence ID that was used to match and find the Hit information in GenBank; a "ProductScore" which provides a measure of the "strength" of a match between the sequence and the public database sequence (obtained from a public database such as GenBank or Blocks); a "Hit_ID" (described below); a "Hit_Type" (described below); a "LogLikelihood" which provides an interpretation of the P-Value for a match between a sequence and a GenBank sequence (i.e., how much better the match is that the hit threshold); a "Hit_DataSource" which provides the name of the public database where the hit was found (e.g., gb103pri); a "Hit_Description_Short" which provides a short description of the hit (e.g., Human anaphylatoxin C3a receptor); an "ExtentValue" which indicates whether or not any coding information is present within the clone (assuming coding sequences (CDS) are noted for the GenBank match; a negative value indicates that the clone's sequence is found more 3' to the CDS); and a "GA_Status" which indicates whether a particular clone is available as a reagent to a third party (customer), and may also contain information indicating whether a reagent clone has been shipped to a customer. Note that a clone may have more than one sequence associated with it, depending upon how the clone was read. For example, a given clone may have three sequences associated with it: a 5' first pass sequence, a 3' first pass sequence, and a 5' long read sequence.

Information regarding each of the sequences associated with the clones in Clone table 304 are stored in a Sequence table 306. The records of Sequence table 306 include a "SequenceID" (primary key); a CloneID (foreign key inherited from Clone table 304); a "Seq_Length" which provides the length of the sequence in base pairs; a "Seq_Description" which provides a limited descriptive information about the sequence; a ProductScore; a Hit_ID; a Hit_Type; a LogLikelihood; a HitDataSource; and, a Hit_Description_Short.

Additional details about matches between public domain genes and the sequences in the Sequence table 306 appear in a "SequenceHit" table 332. The SequenceHit table 332 provides details about one or more hits for a given sequence. Note that a given sequence may have multiple hits in the public databases. The table includes "SequenceID" together with a "HitID" attribute and a "HitType" attribute as a primary key. The HitID attribute lists a unique identifier of the public domain gene (e.g., a GI for GenBank genes) matched with the sequence in question. Sequences that have no matches in the public databases may be flagged as "INCYTE" (for clusters in the Incyte Pharmaceuticals, Inc. LifeSeq® database, for example) or "UNQSGL" (for unique singleton), for example. HitType specifies the general source of a hit in terms such as "g" for a GenBank match, "b" for a Blocks match, and "*" for no external match. "Hit_DataSource" and "Hit_Description" attributes identify the data source of the hit (e.g., GenBank or Blocks) and some information, if any, taken from the public database regarding the hit gene sequence.

Other attributes in SequenceHit table 332 include "LogLikelihood", ProductScore, "Blast_Score", and "Percent_ID", each of which describe a quantitative measure of the match between the clone and the sequence. Details of these measures are provided below. Another attribute provided in this table is "Seq_Direction" which specifies whether the match is made in the same direction (e.g., 3' direction for the public sequence and 3' direction for the internal sequence) or in the complimentary direction (e.g., 3' direction for the public sequence and 5' direction for the internal sequence). Other attributes in table 332 include "Query_Start" and "Query_End" which specify the beginning and end (in base pair numbers) of the internal sequence that matches the public database sequence constituting the hit. Similarly, a "Match_Start" and "Match_End" specify the beginning and end (in base pair numbers) of the public sequence that matches the query (internal) sequence. For example, the Query_Start and Query_End values might be 204 and 263 while the Match_Start and Match_End might be 539 and 598.

Each record in Clone table 304 references multiple clone clusters identified by comparing the clones against existing internal private sequences at varying stringencies (see step 12 of FIG. 1A). The clone cluster records are stored in a "CloneCluster" table 308. Each record in CloneCluster table 308 will reference a single clone record from Clone table 304 and will have as its primary key, a "ClusterID", a "ClusterMethod"(e.g., stringency), and the associated CloneID. CloneCluster table 308 also includes the "Library_ID" (foreign key inherited from Library table 302) and the NumSeqs attribute described above.

Those clone clusters that form master clusters are provided in an "IncyteCluster" table 310. As each master cluster is comprised of unique clusters, each record in IncyteCluster table 310 always groups many clone clusters from table 308. Table 310 includes as its primary key the ClusterID, and "ClusterMethod". Table 310 also includes the Hit_ID, Hit_Type and ProductScore attributes as described above. In addition, the table includes a "RepCloneID" which specifies a representative clone from the cluster. The representative clone is that clone having the highest matching score (e.g., Product Score) versus a public database hit (e.g., a matching sequence found in GenBank). Finally, table 310 includes a "MasterClusterID" which is a foreign key inherited from a "MasterCluster" table 312.

MasterCluster table 312 includes records of all "master clusters" which are comprised of multiple clone clusters (see FIG. 1B). Each Masterluster record references a single master cluster which was obtained by matching two or more clusters (or singletons which form their own clusters) against sequences provided in one or more public databases (e.g., GenBank). MasterCluster table 312 specifies only the MasterClusterID and ClusterMethod (together the primary key). Information about the hits to public database sequences that generated the master clusters is provided in a "MasterClusterHit" table 314. Each record of a master cluster hit in table 314 belongs to exactly one MasterClusterRecord in table 312 and represents a single external hit (referenced in an ExternalHit table 316). As multiple hits are required to make a master cluster, each master cluster in MasterCluster table 312 will contain multiple master cluster hits. Each record of MasterClusterHit table 314 includes the MasterClusterID associated with the hit, the Cluster Method generating the hit, the Hit_ID, and the Hit_Type (all primary and foreign keys).

A "MasterClusterAbun" table 340 provides information about the number of times members of a master cluster appear in a given library. As a primary key, table 340 has Library_ID, MasterClusterID, and ClusterMethod (all are also foreign keys). Abundance data is provided as a "MasterAbun" attribute (raw number of times a particular cluster appears in a library) and "MasterPctAbun" attribute (abundance divided by the total number of usable sequences in the library). In addition, table 340 includes a "CommonGene" attribute which indicates that a particular gene is so universally present that including it in a common set may obscure commonality unique to multiple libraries in a "commonality" comparison. Examples of ubiquitous genes that might be labeled "CommonGene" include actin and the genes encoding proteins used in certain universal cell metabolism pathways. Other fields in the MasterClusterAbun table 340 include Hit_ID, Hit_Type and Annot_SequenceID, which are all foreign keys; ProductScore; "RepCloneID" which provides the representative clone for a master cluster—that is, that clone that matches one of the indexed GIs (via UniGene) with the highest Product Score; Hit_DataSource; and, Hit_Description_Short.

ExternalHit table 316 records include information about each unique hit, regardless of cluster method, used to form master clusters. Thus, each external hit represents multiple master cluster hits. ExternalHit table 316 has as its attributes: Hit_ID, Hit Type, CommonGene, and Hit_Description.

To categorize the master clusters, a "ProteinFunction" table 318 is provided. As discussed in more detail below, ProteinFunction table 318 includes classification hierarchies for enzyme function and protein function. This allows a user to search for all sequences in the gene expression database that are associated with a particular protein or enzyme function.

A "LibraryHit" table 342 includes all hits associated with a given library. It has as its primary key Library_ID, ClusterMethod, Hit_ID, and Hit_Type fields. The table 342 also includes a "LibHitAbun" field, which provides the total number of clones from master clusters with clones that have been assigned hits to a particular GenBank sequence, and a "LibPctAbun field, which provides the percentage that the LibHitAbun number represents of the total number of clones belonging to the library in question.

Protein function table 318 simply includes the classification hierarchy for the protein and enzyme functions (as indicated by "PF_ID" and "PF_Type" primary keys). The PF_Type specifies the hierarchy type (e.g., enzymatic, structural, etc. as explained below). The table also includes a "PF_ParentID" attribute designating a parent classification in the hierarchy, if any, and a "PF_Description" attribute describing the entry (e.g., "potassium channels"). Table 318 references a "PFExternalHit" table 320 which includes records of external hits (from table 316) which have been classified according to a protein function classification as provided in table 318. The PFExternalHit table 320 has PF_ID, Hit_ID, and Hit_Type fields, all of which are primary keys.

To allow clones to be searched by GenBank identifier (GI), Locus Name, and Accession Number, a "GIX_Ref" table 344, a "GILocus" table 346, and a "GIAccession" table 348 are provided. Each of these specify Hit_ID and one other particular identifier. Each record in each of these tables is always represented by one external hit.

Seven tables describing pathological/medical details associated with a tissue, the tissue's donor or a relative of the donor are referenced through Library table 302. As mentioned, Library table 302 inherits the TissueID foreign key from TissueSpecimen table 330. These two tables are related such that each Library tuple references only one tissue specimen, and each TissueSpecimen table references multiple libraries. Other attributes of TissueSpecimen table 330, in addition to TissueID, include a DonorID specifying the tissue specimen's donor (e.g., a human individual), a "TissueType" (e.g., normal, diseased, involved, or cancer) an "Organ" (e.g., liver, heart, appendix), and a "GrossDescription" (measurements: size, weight, etc.). Further, the table includes a "TissueMargin" attribute specifying the tissue margin's appearance such as clean edges (associated with most normal tissue) or jagged edges (associated with some tumors). In addition, each tuple includes a "TissuePrimary" attribute and a "TissueSecondary" attribute which together specify a hierarchy of tissue categories. For example a lung tissue sample may be categorized "left lung" (TissuePrimary) and "bronchiole" (TissueSecondary). In a preferred embodiment, the tissue hierarchy is the SNOMED International Systemized Nomenclature of Human and Veterinarian Medicine from the College of American Pathologists.

Each tissue specimen (as uniquely identified by TissueID) may have many "diagnoses" as specified in a TissueDiagnosis table 350. This table has as its primary key TissueID in conjunction with "Diagnosis". Multiple diagnoses for a given tissue might include "old" and "melanoma" for example.

Each tissue specimen record belongs to a single donor, and each donor may provide many tissue specimens. Donor information is provided in a "DonorSnapshot" table 352 which has as its primary key DonorID in conjunction with "RelationNumber" and "RelationType". Obviously, DonorID uniquely specifies the tissue donor. However, in order to trace a family history of the donor, certain information about the donor's family members may also be provided. Thus, in some records of DonorSnapshot table 352, RelationType will specify father, mother, sibling, grandparents, etc. It may also specify "SELF". The RelationNumber may be 1, 2, . . . to, for example, distinguish between a first sibling, a second sibling, and so on. DonorSnapshot table 352 also specifies a "Species" (human, mouse, bacteria, etc.), a "DevelopmentStage" (adult, fetal, infant, cell line, etc.), an "Age", a "Weight", a "Height", a "Sex", a "Race", and a "CauseOfDeath".

Each DonorSnapshot record may have associated therewith many "social history" records in a "SocialHistory" table 354. This table has as its primary key DonorID and RelationNumber and it includes such information as drug and alcohol dependence, smoker, etc. This information is provided by an "Item" attribute (e.g., alcohol dependence), a "Descriptor" attribute (e.g., beer or hard liquor), and a "Status" attribute (e.g., past or active).

To account for the effects of any medication taken by a donor, a "Medication" table 356 is provided. Each DonorSnapshot record may have many medications. Medication table 356 has as its primary key DonorID and RelationNumber. The medication taken by the donor is specified by the following attributes: "GenericName" (e.g., nitroglycerin, digitalis), "MedicationGroup" (e.g., cardiovascular agent), and "SubGroup" (e.g., anti-anginal agent). The table also specifies Status (e.g., past or active).

Further information about the donor may be provided in a "MedicalHistory" table 358 having as its primary key DonorID and RelationNumber. Each donor record may have multiple medical histories. MedicalHistory table 358 specifies a "Problem" (e.g., breast cancer), a "HistGroup" (e.g., neoplasm), and "SubGroup" (e.g., breast). In addition, table 358 specifies the "Status" of the medical history, such as past or active.

Finally, a "MedProcedure" table 360 may specify one or more medical procedures performed on the donor. Again the primary key is DonorID and RelationNumber. The attributes provided include the following: a "MedProcedure" (e.g., appendectomy), a "ProcedureGroup" (e.g., operative procedure or in house procedure), a "SubGroup" (e.g., gastrointestinal procedure, dermal procedure, etc.), and a "Complication" (e.g., post operative bleeding or infection). Finally, the table includes a "Status" attribute.

A GA_Sequences table contains fields for information obtained from nominated clones which have been resequenced and made part of the reagent set in accordance with the present invention. A SequenceID (primary key) identifies sequences associated with a reagent clone. Since a reagent clone has been resequenced, it has a plurality of sequences (e.g., 5' and 3' long read sequences), in addition to its EST, associated with it. The database of the present invention supports the association of a plurality of sequences with a clone. A reagent clone is identified by a CloneID (foreign key inherited from Clone table 304 via the GA_Well table 375). A Seq_Length field provides the length of a given sequence in base pairs, a SeqDescription field provides limited descriptive information about the sequence, and a SequenceType field indicates whether the sequence was a 5' or 3' and a short or long read. A Hit_ID field lists a unique identifier of the public domain gene (e.g., a GI for GenBank genes) matched with the sequence in question. Sequences that have no matches in the public databases may be flagged as "INCYTE" (for clusters in the Incyte Pharmaceuticals, Inc. LIFESEQ™ database, for example) or "UNQSGL" (for unique singleton), for example. Hit_Type specifies the general source of a hit in terms such as "g" for a GenBank match, "b" for a Blocks match, and "*" for no external match. Hit_DataSource and Hit Description fields identify the data source of the hit (e.g., a GenBank division such as Primate or Rodent) and some information, if any, taken from the public database regarding the hit gene sequence. Blast Score, Blast Pvalue and Blast PctIdentity fields contain information describing a quantitative measure of the match between the clone and the sequence. An Accession field provides a GenBank accession number for a hit. A Primer field provides the primer type used for sequencing (e.g., TN Wobble or M13-R).

The GA_Sequence table is linked to the GA_Well table 375 through their common CloneID foreign key inherited from Clone table 304. The GA_Well table 375 includes fields for information relating to the nature and location of a reagent clone. The table 375 includes a LotID, which identifies the lot where a reagent clone is located, and a WellID which provides the address of the well in the lot where the clone is located. A CloneID identifies the clone that is in a given lot and well. A Vector field identifies the type of cloning vector used, and the Insertion Site identifies the restriction site(s) in the vector where a clone sequence is inserted. A SequenceSizeCut field provides the size of the clone sequence insert, as estimated by gel electrophoresis.

The GA_LotInformation table 380 provides information relating to a particular reagent lot. A LotID field identifies the lot (e.g., the 96-well plate) where a reagent clone is located. A Barcode field provides a barcode value for the part number and lot number of a reagent shipment. A CustomerID field contains information that identifies a customer and site to which a shipment was sent (for example, "Cust1-PA" or "Cust1-StL" for a customer abbreviated as Cust1 at its Palo Alto and St. Louis sites, respectively). A Date Shipped field provides the date a shipment was sent to a customer. And a Comments field is available for comments regarding a lot.

5. The Reagent Information User Interface

The data acquisition and population of the reagent information database of a preferred embodiment of the present invention have been described above. From this description, one of ordinary skill in the art will understand that the database contains records relating to sequence and reagent data relating to a plurality of clones, including reagent clones, as described above. The database thus serves as a reference for identification and tracking of reagent clones and provides the capacity to do sequence analysis on these clones. The database provides a user interface to allow a user to access the data stored in the relational reagent information database. A preferred embodiment of this user interface is described below.

Figure 4A:
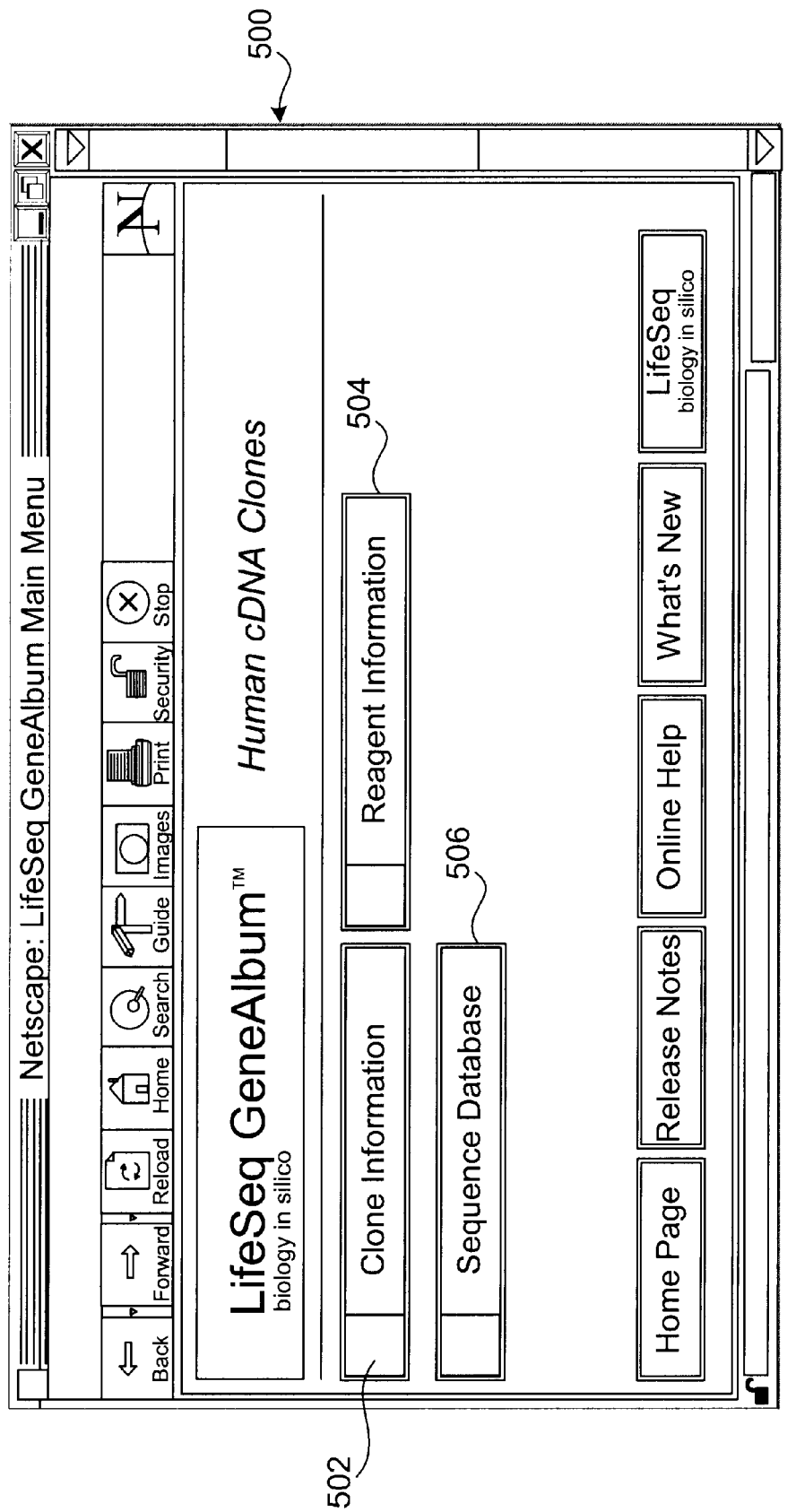

In a preferred embodiment, the database system of the present invention provides an HTML graphical user interface. The user interface preferably has three principal features. Clone Information screens allow a user to query and receive results about the availability of reagent clones, and Reagent Information screens provide the ability to query on and display information about lots and clones. Both of these user interface screens are used to access the relational database (reagent database) described above. Referring to FIG. 4A, a main menu (cDNA Clones) screen 500 for the database of the present invention is shown. This main menu screen 500 may be accessed through an interface that provides access to a sequence (e.g., EST) database to which the present invention is appended. The main menu screen 500 provides Clone Information 502 and Reagent Information 504 buttons, which may be selected by clicking with a mouse, to access screens relating to either type of information stored in the relational database. The third feature of the user interface is that it provides access to a Sequence Database (by clicking on Sequence Database button 506 in main menu screen 500) which contains flat files of FASTA-formatted sequence data. The Sequence Database is described in Provisional Patent Application Ser. Nos. 60/040,033 and 60/040,033 and patent application Ser. No. 08/947,845 previously incorporated by reference herein, and will not be described further in this application.

Figure 4B:
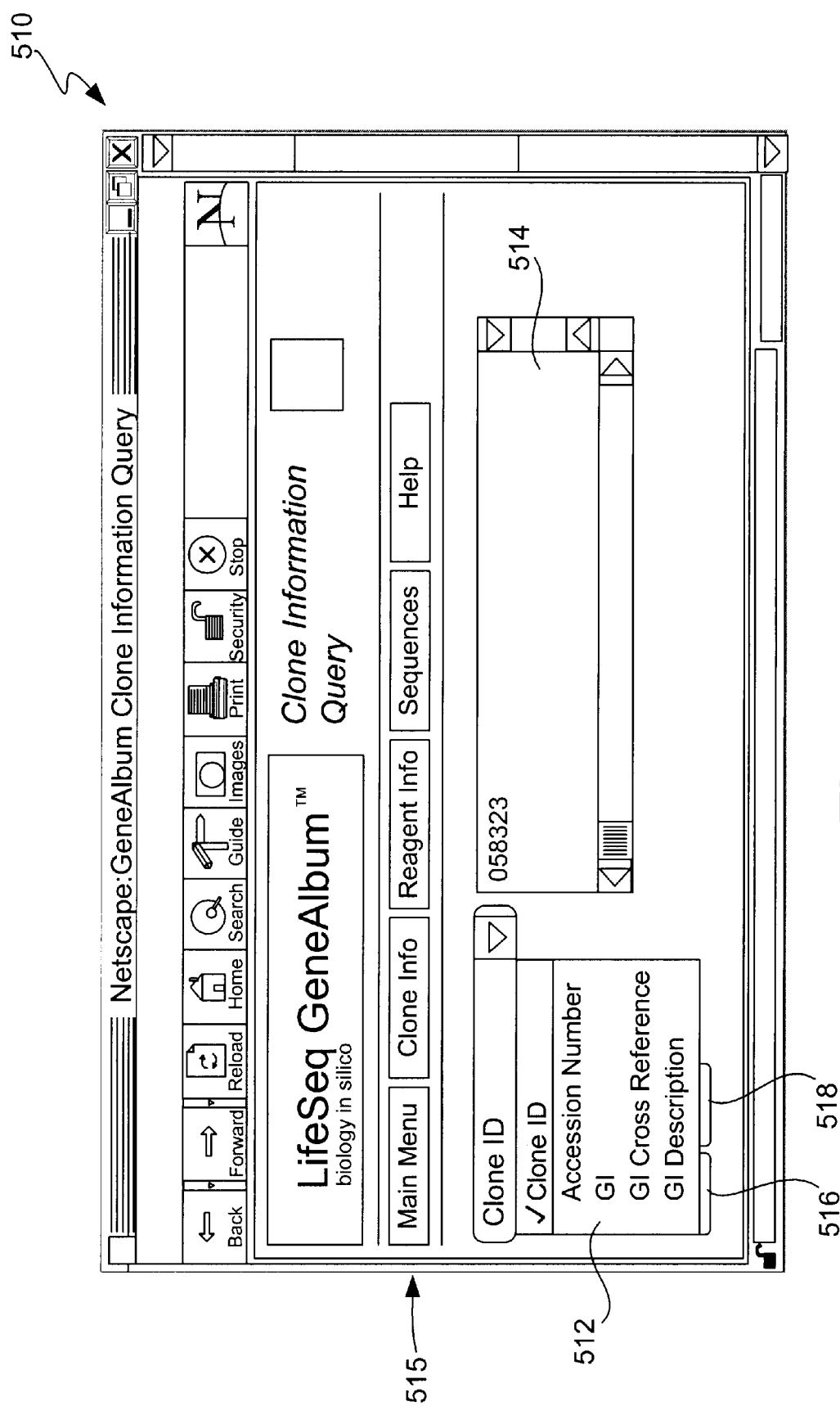

If a user selects the Clone Information button 502 in the main menu screen 500, a Clone Information Query screen 510 is returned, as shown in FIG. 4B. To perform a Clone Information Query, a user selects a search criteria category from a pull-down menu 512 and enters a search query in a text box 514. The available search criteria categories are Clone ID, Accession Number, GI, GI Cross Reference, and GI Description. For the Clone ID search criteria category, a user enters a Clone ID number. For Accession Number, a user enters a GenBank Accession number. For GI number, a user enters a GenBank Identifier (GI) number. For GI Cross Reference, a user enters a GI number. And for GI Description, a user enters a word or phrase. Once the search query has been entered, the user may select the "Search" button 516 (partially obscured in FIG. 4B by the activated pull-down menu 512) to initiate the search.

Note that the Clone Information Query screen 510 "Clear" button 518 (partially obscured in FIG. 4B by the activated pull-down menu 512) allowing users to clear a previous query from the text box 514. Query screen 510 also includes a row of buttons 515 allowing the user to directly transition to a query screen for any of the subjects available through the main menu (e.g., Clone Information ("Clone Info"), Reagent Information (Reagent Info), and Sequence Database ("Sequences")). In addition, the user can return to the main menu by selecting a "Main Menu" button from the row of buttons 515. Further, the user can receive on line help by selecting a "Help" button from row 515. A Clear button equivalent to Clear button 518 appears in each query screen, and a row of buttons equivalent to row 515 appears in each screen of the user interface aspect of the present invention. Finally, the user may exit the program at any time by exiting the browser which supports the interface.

Figure 4C:
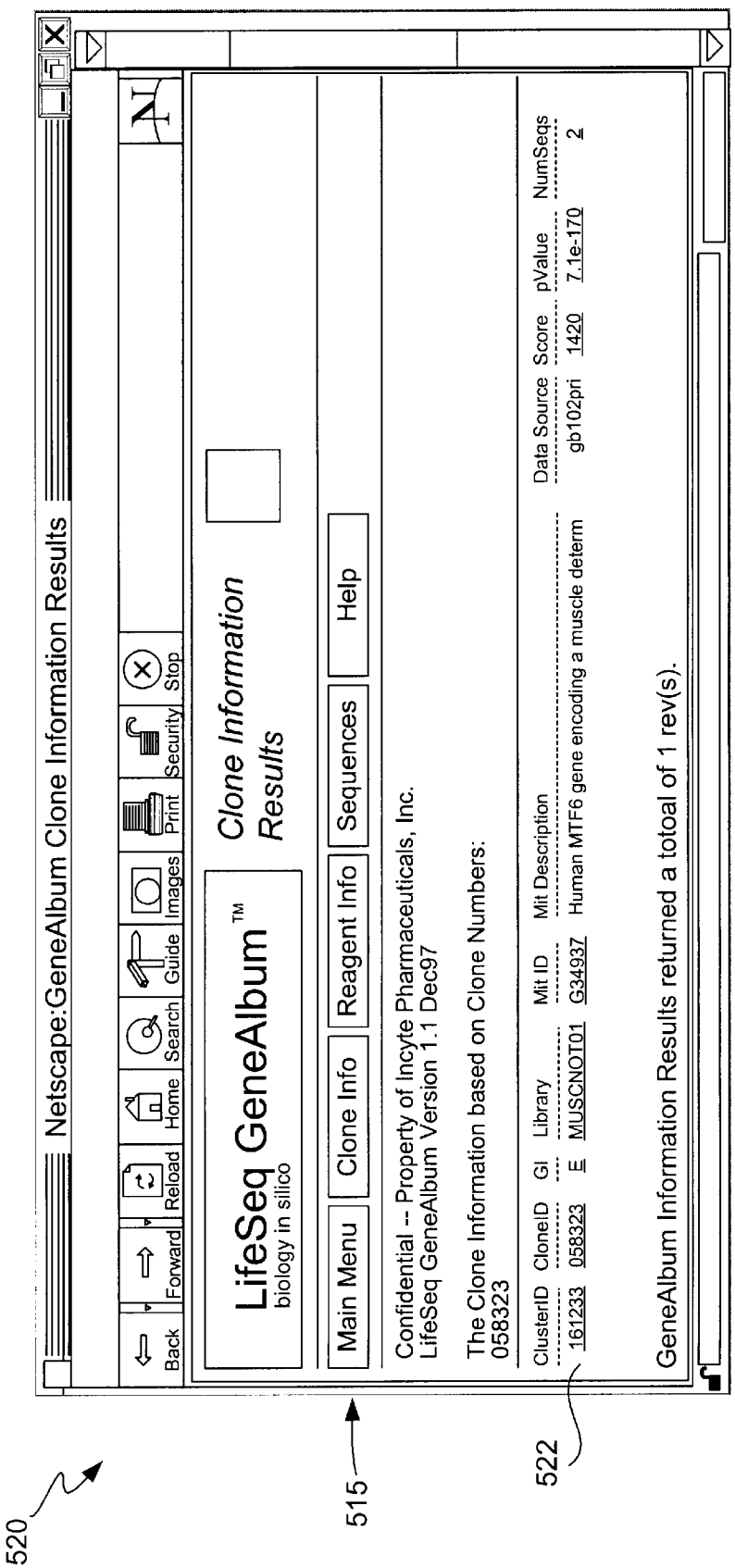

The results of a Clone Information query are displayed in a Clone Information Results screen 520, as shown in FIG. 4C, and consist of a one-line entry for each reagent clone that satisfies the search criteria, such as line 522. The information returned for each clone includes the ID of the Cluster to which that clone belongs, the Clone ID itself, a status field indicating whether the customer has received this clone, the cDNA library from which the clone was obtained, and the number of sequences that were obtained from the clone. Additionally, for clones with annotated 5' sequences, the entry line also includes the GenBank Hit ID with which the clone's 5' sequence was annotated, the Hit Description, the Hit Data Source (e.g., gb104pri, gb10449dp, etc.), and the BLAST Score and P-Value for that hit. The results returned for each search criteria category are as follows: A Clone ID query returns information for the clone matching the ID; An Accession Number query or a GI query returns information for all clones that have a 5' sequence annotated against the GenBank sequence described by that Accession Number or GI number; A GI Cross-Reference query returns information on all clones whose 5' sequences are annotated against a GI number that is in the same cross-referencing group as the query GI (i.e., this returns all annotated sequences in the database for a gene as long as the GI numbers are in the Cross-Referencing table); A GI Description query returns information on all clones that have 5' sequences with that word or phrase in their GI description line.

Entries in this and other results screens may provide links (e.g., via an HTML link) to other information in the database. Such information is indicated by underlining on the pertinent value.

Figure 4D:
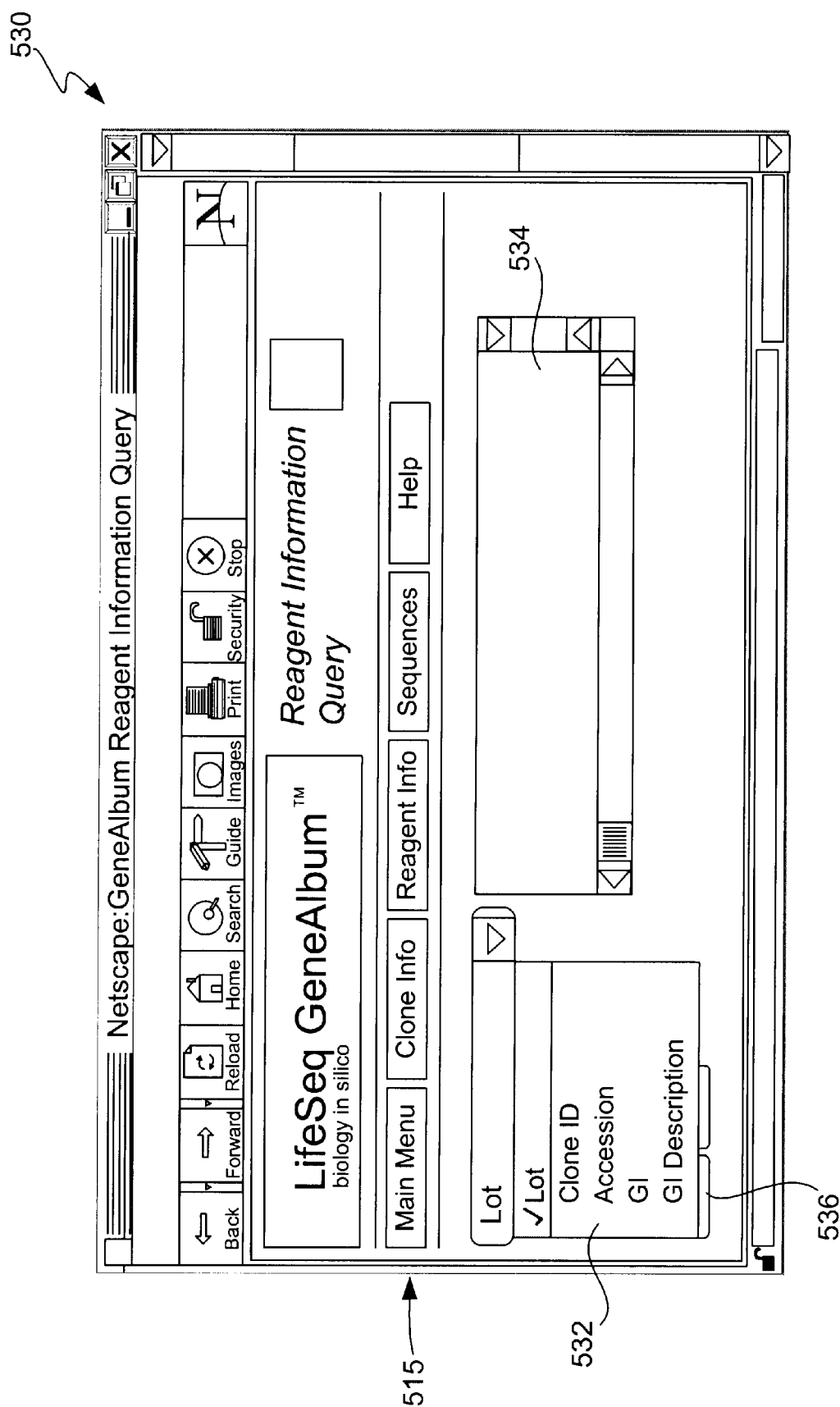

A user may also select the Reagent Information button 504 in the main menu screen 500, to return a Reagent Information Query screen 530, as shown in FIG. 4D. To perform a Reagent Information Query, a user selects a search criteria category from a pull-down menu 532 and enters a search query in a text box 534. The available search criteria categories are Lot, Clone ID, Accession, GI, and GI Description. For the Lot search criteria category, a user enters a Lot ID number identifying a reagent clone lot. For the Clone ID search criteria category, a user enters a clone number identifying an internal or public clone. For Accession, a user enters a GenBank Accession number. For GI, a user enters a GenBank Identifier (GI) number. And for GI Description, a user enters a word or phrase. Once the search query has been entered, the user may select the "Search" button 536 (partially obscured in FIG. 4D by the activated pull-down menu 532) to initiate the search.

The results of a Reagent Information query may be displayed in a Reagent Information Results screen 540, as shown in FIG. 4E. The results displayed for each search criteria category are as follows: A Lot query result displays information about all clones in that lot; a Clone ID query result displays information about the clone and the lot in which the clone is found; an Accession query or a GI query result displays all clones that have a 5' sequence with a match to the entered Accession or GI number; a GI Description query result displays all clones that have a 5' sequence with that word or phrase in their GI description line. The results are displayed in screen 540 in result entry lines, such as line 542. The result entries may provide links to various other screens in the reagent information user interface or in the associated sequence (e.g., EST/gene expression) database showing related information.

Figure 4F:
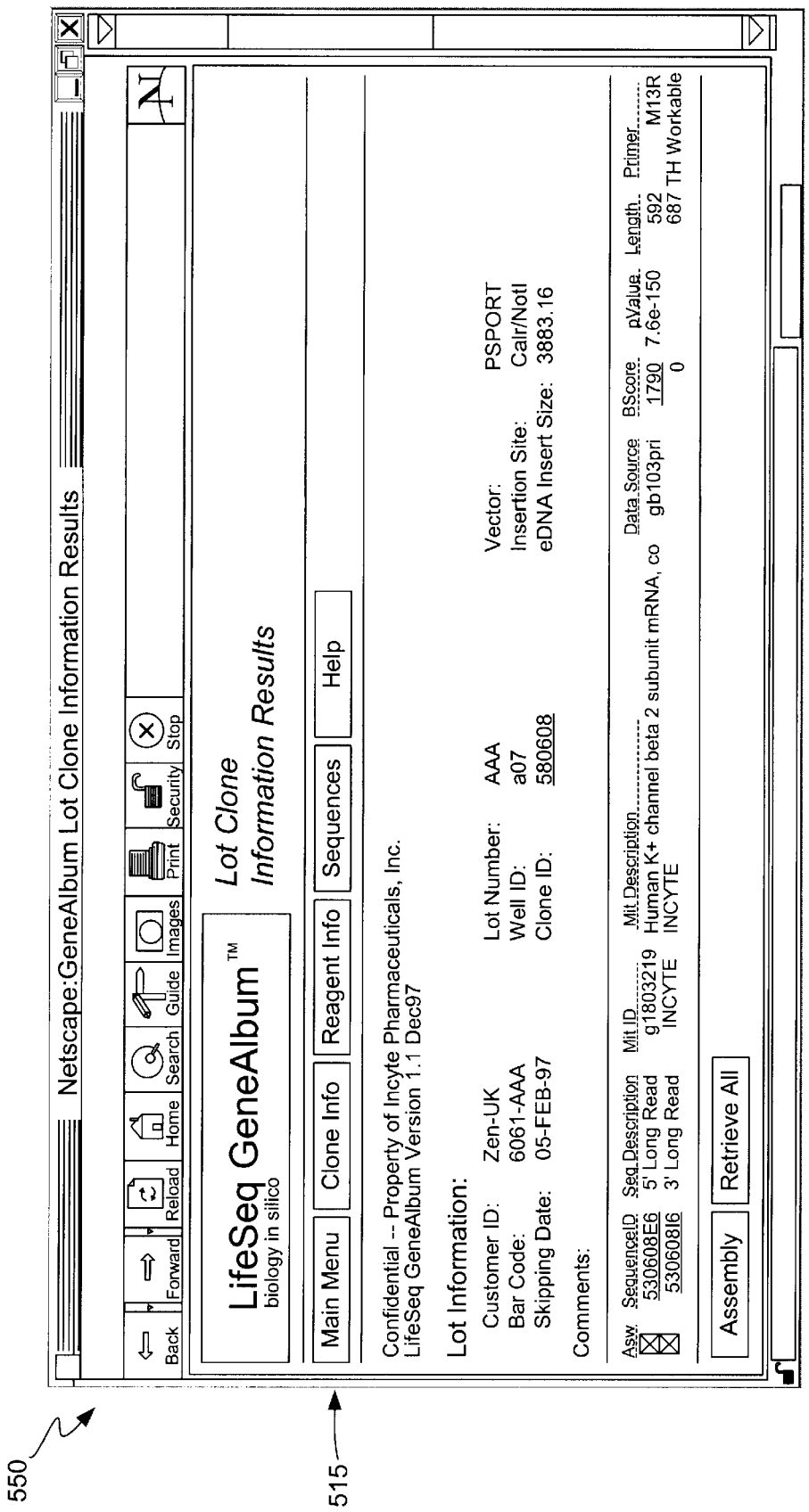

Among the screens that may be accessible by link from the Reagent Information results screen 540, is a Lot Clone Information Results screen 550, such as shown in FIG. 4F. In a preferred embodiment, the Lot Clone Information Results screen 550 is accessed by clicking on the well link of a result entry line (such as well link 544 of result entry line 542) in the Reagent Information results screen 540. The Lot Clone Information Results screen 550 displays information about a reagent clone such as preparation techniques and shipping details. The screen 550 also displays information about the sequences in the relational database associated with the clone, and provides the ability to assemble some or all of these associated sequences into a contiguous sequence.

Figure 4G:
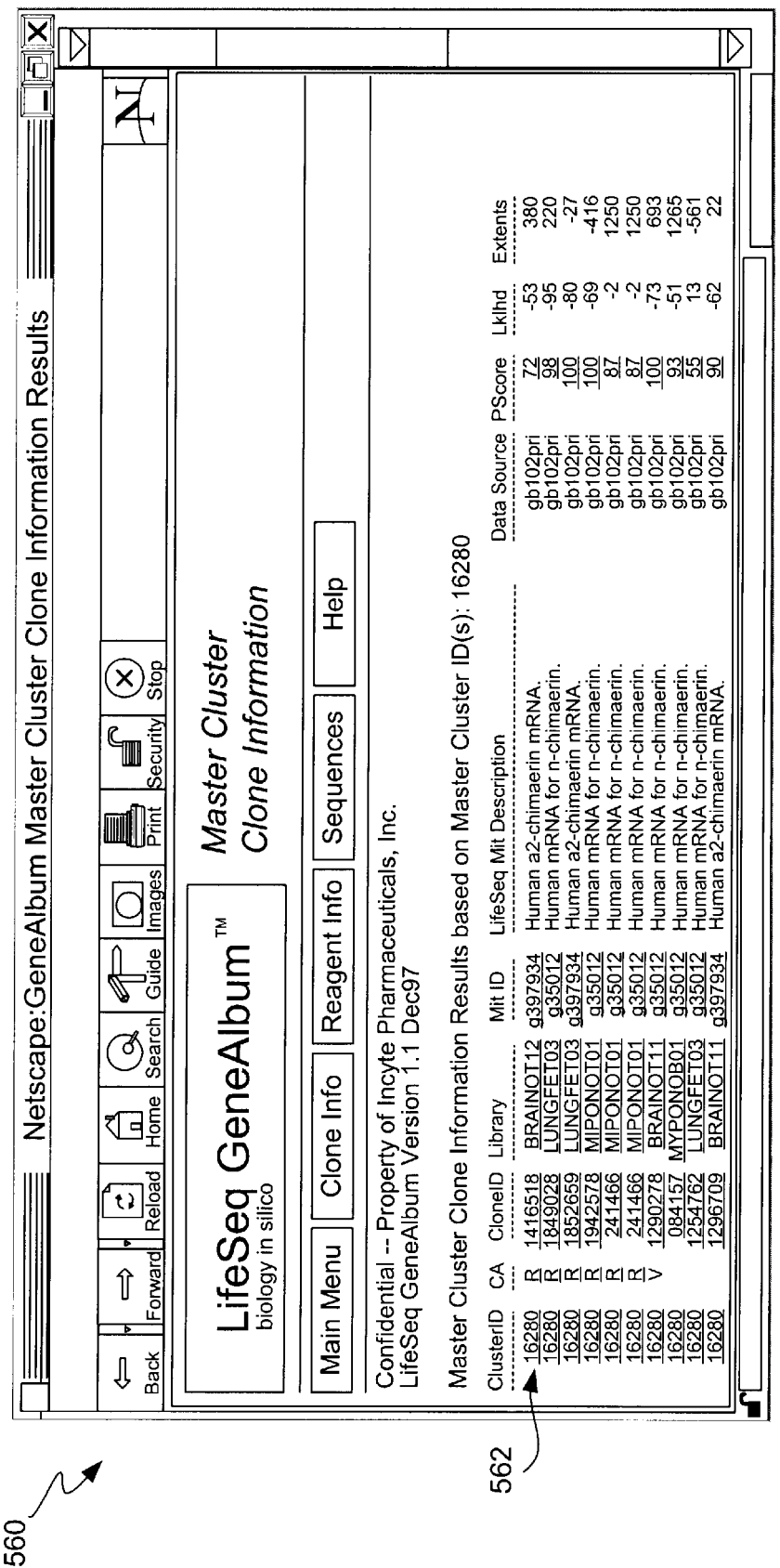

In addition, a MasterCluster Clone Information Screen 560, such as is illustrated in FIG. 4G, may be accessed from a button or link in a screen of the associated sequence database (e.g., the GA MCluster Info button in the Master Cluster Information Screen of Incyte's LifeSeq® database). The screen 560 displays a one-line entry (e.g., 562) for each clone in a LifeSeq Master Cluster. Each entry consists of the following fields: the Cluster ID of the cluster to which the clone belongs, a GA field (described below), the Clone ID, the Library ID for the Library from which that clone was obtained, and a Hit ID (e.g., a GenBank GI number, or, "INCYTE" for unique sequences). Additionally, for clones with a LifeSeq® EST sequence annotated against GenBank, the Hit Description, DataSource, PScore, Lklhd, and Extents fields will be populated with the appropriate information for the LifeSeq® EST sequence's hit. For the GA field mentioned above, a "V" indicates that a clone has been verified and is a reagent available for purchase, and an "R" indicates a clone that has been shipped to the customer. The "R" hypertext link will take the user to the Reagent Information Results screen (FIG. 4E) for that clone.

Figure 5:
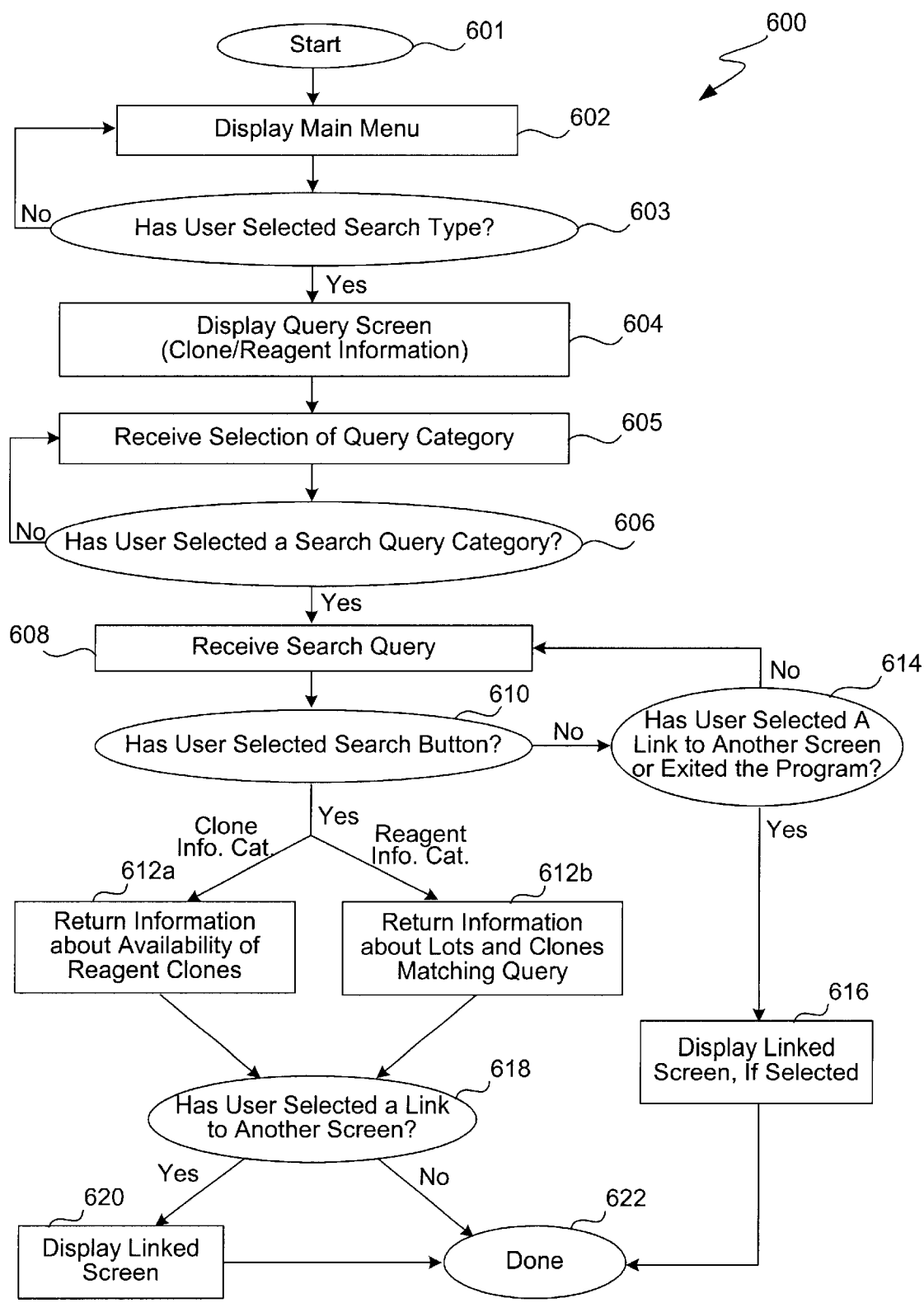
FIG. 5 is a process flow diagram of the steps employed to perform queries of a reagent information relational database using a user interface in accordance with a preferred embodiment of the present invention.

FIG. 5 presents a process flow 600 for the preferred reagent information user interface of the relational database system invention, described above. Those of skill in the art will recognize that other process flows are possible without departing from the spirit and scope of the present invention. The process flow illustrates aspects of the user interface process for accessing the reagent information relational database of the present invention, making reference to the screen shots depicted in FIGS. 5A–F. The process begins at 601 and in a step 602 the system displays a main menu screen 500. As noted above, this main menu screen 500 may be accessed through an interface that provides access to a sequence (e.g., EST) database to which the present invention is appended.

In a step 603, the system determines whether the user has selected a search type by clicking on either the Clone Information 502 or Reagent Information 504 buttons in screen 500. If so, the system displays the appropriate query screen 510 or 530 in a step 604. If not, and the user has made no other selections (this situation is addressed generally below) the system continues to display the main menu screen 500.

In a step 605 the system receives a selection of a particular search query category. As previously noted, each search type has several categories of search queries, e.g., Clone ID, Lot, GI Number, etc. Once the search query type has been selected at step 605, the system determines, at a decision step 606, whether the user has selected a particular search query category. A user may select a category from a pull-down menu 512. If the user has selected a search query category, a search query text box 514 in the user interface is ready to receive a search query. Typically, a user will enter a search query associated with the search query category selected from pull-down menu 512.

Once the search query has been received at step 608, the system determines, at a decision step 610, whether the user has selected a search button in the user interface (or otherwise initiated a search). When the search button has been selected the system returns the information associated with the selected search type, category and query. Where the Clone Information search type was selected at step 603, the system returns information about the availability of reagent clones in result screen 520 at step 612a. Where the Reagent Information search type was selected at step 603, the system returns information about lots and clones which the customer has received that match the query in result screen 540 at step 612b. Steps 612a and 612b are alternative steps based on the preceding search type selection.

As noted above, the system allows the user to exit from a query at any time. The user may take this route by exiting the program or selecting a screen unrelated to the query from among the various buttons 515 provided in the various query and results screens. This option is depicted at a decision step 614 where the system determines whether the user has selected a link to another screen or exited the program. For purposes of illustration, this step is performed after decision step 610 is answered in the negative. Process control is shown returning to step 608 when decision step 614 is answered in the negative. If decision step 614 is answered in the affirmative (i.e., the user elected to leave the query mode), the system displays the linked screen if necessary at a step 616.

The loop including steps 610, 608 and 614 is provided primarily for purposes of illustration. It should be understood that the invention is not limited to this arrangement (or any polling procedure) and may merely await receipt of an appropriate event from the user interface, for example. Moreover, this step could equally well have been depicted anywhere in the flow of process 600.

Also as noted above, various links (preferably HTML links) to additional related screens may also be provided in addition to the buttons 515, such as those illustrated in result line 542 of result screen 540 of FIG. 4E (Reagent Information Results screen). This feature is depicted at a decision step 618 where the system determines whether the user has selected a Hypertext link to another screen. This step is performed following the display of the search results in the Clone Information 520 or Reagent Information 540 results screens at step 512. A user may select (e.g., by clicking) a Hypertext link (e.g., one indicated by underlining or highlighting) in order to access linked information in the database. If decision step 618 is answered in the affirmative (i.e., the user selected a Hypertext link), the system displays the linked screen at a step 620. The Lot Clone Information Results screen 550 illustrated in FIG. 4F is an example of a screen accessed via a link from another screen in the interface.

Following the return of query results or the selection of another screen in any of steps 616, 618 and 620, the process is then completed at 622.

9. Conclusion

Although a few specific embodiments of the present invention have been described in detail, for purposes of clarity of understanding, it will be apparent that certain changes and modifications may be practiced within the scope of the appended claims. It should be noted that there are many alternative ways of implementing both the process and database system of the present invention. Accordingly, the present embodiments are to be considered as illustrative and not restrictive, and the invention is not to be limited to the details given herein, but may be modified within the scope and equivalents of the appended claims.

What is claimed is:

1. A computer system, comprising:
    a relational database having
        (i) records containing information identifying sequences of a plurality of reagent clones, wherein said reagent clones have been nominated based on specified priority criteria, and
        (ii) records containing information identifying reagent information accumulated in sequencing and verification of said plurality of reagent clones, wherein verification comprises using laboratory processes to verify that said plurality of reagent clones is viable; and
    a user interface allowing a user to selectively access the information contained in the records.

2. The computer system of claim 1, wherein said records are organized into a plurality of tables.

3. The computer system of claim 1, wherein the regent information includes physical data and ordering information for said clones.

4. The computer system of claim 3, wherein said physical data and ordering information for a clone includes the clone's processing history, availability, and location.

5. The computer system of claim 1, wherein said clones are cDNA clones.

6. A computer system, comprising:
    a relational database having
        (i) records containing information identifying sequences with associated information from a relational gene sequence database,
        (ii) records containing information identifying sequences of a plurality of reagent clones that have been nominated from said gene sequence database based on specified priority criteria, and
        (iii) records containing information identifying reagent information accumulated in sequencing and verification of said reagent clones, wherein verification comprises using laboratory processes to verify that said plurality of reagent clones is viable; and
    a user interface allowing a user to selectively access the information contained in the records.

7. The computer system of claim 6, wherein said records are organized into a plurality of tables.

8. The computer system of claim 6, wherein the information includes physical data and ordering information for said reagent clones.

9. The computer system of claim 8, wherein said physical data and ordering information for a clone includes the clone's processing history, availability, and location.

10. The computer system of claim 6, wherein said clones are cDNA clones.

11. A method, implemented on a computer system, for accessing information relating to one or more reagent clones, comprising:
    providing a relational database having
        (i) records containing information identifying sequences of a plurality of reagent clones, wherein said reagent clones have been nominated based on specified priority criteria, and
        (ii) records containing information identifying reagent information accumulated in sequencing and verification of said plurality of reagent clones, wherein verification comprises using laboratory processes to verify that said plurality of reagent clones is viable;
    entering, in a graphical user interface, a query relating to the information contained in the records;
    determining matches between said query entry and said information; and
    displaying the results of said determination.

12. The method of claim 11, wherein the reagent information includes physical data and ordering information for said clones.

13. The method of claim 12, wherein said physical data and ordering information for a clone includes the clone's processing history, availability, and location.

14. The method of claim 11, wherein said clones are cDNA clones.

15. A method, implemented on a computer system, for accessing information relating to one or more reagent clones, comprising:
    providing a relational database having (i) records containing information identifying sequences with associated information from a relational gene sequence database, (ii) records containing information identifying sequences of a plurality of reagent clones that have been nominated from said relational gene sequence database based on specified priority criteria, and (iii) records containing information identifying reagent information accumulated in sequencing and verification of said reagent clones, wherein verification comprises using laboratory processes to verify that said plurality of reagent clones is viable;

entering, in a graphical user interface, a query relating to the information contained in the records;

determining matches between said query entry and said information; and displaying the results of said determination.

16. The method of claim 15, wherein the reagent information includes physical data and ordering information for said reagent clones.

17. The method of claim 16, wherein said physical data and ordering information for said reagent clones includes the clone's processing history, availability, and location.

18. The method of claim 15, wherein said clones are cDNA clones.

19. A computer program product, comprising a computer-usable medium having computer-readable program code embodied thereon relating to a relational database (i) records containing information identifying sequences of a plurality of reagent clones, wherein said reagent clones have been nominated based on specified priority criteria, and (ii) records containing information identifying reagent information accumulated in sequencing and verification of said plurality of reagent clones, wherein verification comprises using laboratory processes to verify that said plurality of reagent clones is viable.

20. The computer program product of claim 19, wherein the reagent information includes physical data and ordering information for said clones.

21. The computer program product of claim 20, wherein said physical data and ordering information for a clone includes the clone's processing history, availability, and location.

22. The computer program product of claim 19, wherein said clones are cDNA clones.

23. A computer program product, comprising a computer-usable medium having computer-readable program code embodied thereon relating to a relational database having (i) records containing information identifying sequences with associated information from a relational gene sequence database, (ii) records containing information identifying sequences of a plurality of reagent clones that have been nominated from said relational gene sequence database based on specified priority criteria, and (iii) records containing information identifying reagent information accumulated in sequencing and verification of said reagent clones, wherein verification comprises using laboratory processes to verify that said plurality of reagent clones is viable.

24. The computer program product of claim 23, wherein the reagent information includes physical data and ordering information for said clones.

25. The computer program product of claim 24, wherein said physical data and ordering information for a clone includes the clone's processing history, availability, and location.

26. The computer program product of claim 23, wherein said clones are cDNA clones.

27. A computer program product, comprising a computer-usable medium having computer-readable program code embodied thereon relating to a relational database having (i) records containing information identifying sequences of a plurality of reagent clones, wherein said reagent clones have been nominated based on specified priority criteria, and (ii) records containing information identifying reagent information accumulated in sequencing and verification of said plurality of reagent clones, wherein verification comprises using laboratory processes to verify that said plurality of reagent clones is viable;

the computer program product comprising computer-readable program code for effecting the following steps within a computing system:

providing an interface for receiving a query relating to the information contained in the records;

determining matches between said query entry and said information; and displaying the results of said determination.

28. The computer program product of claim 27, wherein the reagent information includes physical data and ordering information for said clones.

29. The computer program product of claim 28, wherein said physical data and ordering information for a clone includes the clone's processing history, availability, and location.

30. The computer program product of claim 27, wherein said clones are cDNA clones.

31. A computer program product, comprising a computer-usable medium having computer-readable program code embodied thereon relating to a relational database having (i) records containing information identifying sequences with associated information from a relational gene sequence database, (ii) records containing information identifying sequences of a plurality of reagent clones that have been nominated from said relational gene sequence database based on specified priority criteria, and (iii) records containing information identifying reagent information accumulated in sequencing and verification of said reagent clones, wherein verification comprises using laboratory processes to verify that said plurality of reagent clones is viable;

the computer program product comprising computer-readable program code for effecting the following steps within a computing system:

providing an interface for receiving query relating to the information contained in the records;

determining matches between said query entry and said information; and displaying the results of said determination.

32. The computer program product of claim 31, wherein the reagent information includes physical data and ordering information for said clones.

33. The computer program product of claim 32, wherein said physical data and ordering information for a clone includes the clone's processing history, availability, and location.

34. The computer program product of claim 31, wherein said clones are cDNA clones.

35. A method, at least partially implemented on a computer system, for establishing a set of reagent clones, comprising:

grouping initial sequences of polynucleotide inserts in a plurality of clones into a master cluster;

assembling the initial sequences of the master cluster into one or more contiguous sequences, such that relationships of sequences to each other in the master cluster are elucidated;

nominating at least one clone represented by a master cluster as a reagent clone, according to specified priority criteria and verifying the quality of the reagent clone by laboratory processes, wherein said laboratory processes comprise verifying that the reagent clone is viable and can grow to amounts suitable for isolating the clone's polynucleotide insert sequence; and sequencing said clone's polynucleotide insert sequence using 5' and 3' long read sequencing, wherein said priority criteria comprise:
(1) a clone associated with a 5'-most initial sequence in an assembly;
(2) a clone having an insert in a pINCY vector, such that if the 5'-most clone in the assembly is not a pINCY clone, the 5'-most pINCY clone is nominated if it is no more than 150 bases shorter than the 5'-most clone; and
(3) if the polynucleotide sequences of a cluster do not assemble, then the most recently sequenced clone insert in a pINCY vector is nominated.

36. A reagent clone identified by a process, at least partially implemented on a computer system, for establishing a set of reagent clones, comprising:

grouping initial sequences of polynucleotide inserts in a plurality of clones into a master cluster;

assembling the initial sequences of the master cluster into one or more contiguous sequences, such that relationships or sequences to each other in the master cluster are elucidated; and nominating at least one clone represented by a master cluster as a reagent clone, according to specified priority criteria wherein said priority criteria comprise:
(1) a clone associated with a 5'-most initial sequence in an assembly;
(2) a clone having an insert in a pINCY vector, such that is the 5'-most clone in the assembly is not a pINCY clone, the 5'-most pINCY clone is nominated if it is no more than 150 bases shorter than the 5'-most clone; and
(3) if the polynucleotide sequences of a cluster do not assemble, then the most recently sequenced clone insert in a pINCY vector is nominated.

* * * * *